United States Patent
Shinde et al.

(10) Patent No.: US 11,034,703 B2
(45) Date of Patent: Jun. 15, 2021

(54) PROCESS FOR PREPARING CHIRAL 2,3-DIHYDROTHIAZOLO[3,2-A] PYRIMIDIN-4-IUM COMPOUNDS

(71) Applicant: BASF SE, Ludwigshafen am Rhein (DE)

(72) Inventors: Harish Shinde, Navi Mumbai (IN); Christopher Koradin, Ludwigshafen (DE); Joachim Dickhaut, Ludwigshafen (DE); Roland Goetz, Ludwigshafen (DE); Eric George Klauber, Huntsville, AL (US); Sukunath Narayanan, Ludwigshafen (DE); Dhanyakumar Raut, Navi Mumbai (IN)

(73) Assignee: BASF SE, Ludwigshafen (DE)

( * ) Notice: Subject to any disclaimer, the term of this patent is extended or adjusted under 35 U.S.C. 154(b) by 48 days.

(21) Appl. No.: 16/610,186

(22) PCT Filed: May 2, 2018

(86) PCT No.: PCT/EP2018/061094
§ 371 (c)(1),
(2) Date: Nov. 1, 2019

(87) PCT Pub. No.: WO2018/202654
PCT Pub. Date: Nov. 8, 2018

(65) Prior Publication Data
US 2021/0087207 A1 Mar. 25, 2021

(30) Foreign Application Priority Data
May 3, 2017 (EP) ..................... 17169294

(51) Int. Cl.
*C07D 513/04* (2006.01)
*C07D 417/04* (2006.01)
*C07D 401/04* (2006.01)
*C07D 403/04* (2006.01)
*C07D 419/04* (2006.01)
*C07C 403/04* (2006.01)

(52) U.S. Cl.
CPC .......... *C07D 513/04* (2013.01); *C07C 403/04* (2013.01); *C07D 401/04* (2013.01); *C07D 417/04* (2013.01); *C07D 419/04* (2013.01); *C07B 2200/07* (2013.01)

(58) Field of Classification Search
CPC .. C07D 513/04; C07D 417/04; C07D 419/04; C07D 401/04; C07D 403/04; C07B 2200/07
See application file for complete search history.

(56) References Cited

U.S. PATENT DOCUMENTS

2020/0055872 A1   2/2020   Shinde et al.

OTHER PUBLICATIONS

U.S. Appl. No. 16/608,290, filed Oct. 25, 2019, Harish Shinde et al.

*Primary Examiner* — Susanna Moore
(74) *Attorney, Agent, or Firm* — Marshall, Gerstein & Borun LLP

(57) ABSTRACT

The present invention relates to a process for preparing optically active compounds of formula X and intermediates thereof,

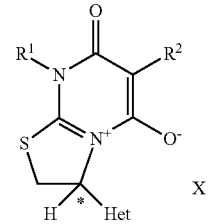

wherein the variables of compound of formula X are as defined in the claims and the description.

16 Claims, No Drawings

PROCESS FOR PREPARING CHIRAL 2,3-DIHYDROTHIAZOLO[3,2-A] PYRIMIDIN-4-IUM COMPOUNDS

The present invention relates to a process for preparing S-containing pyrimidinium compound of formula X according to the following reaction sequence:

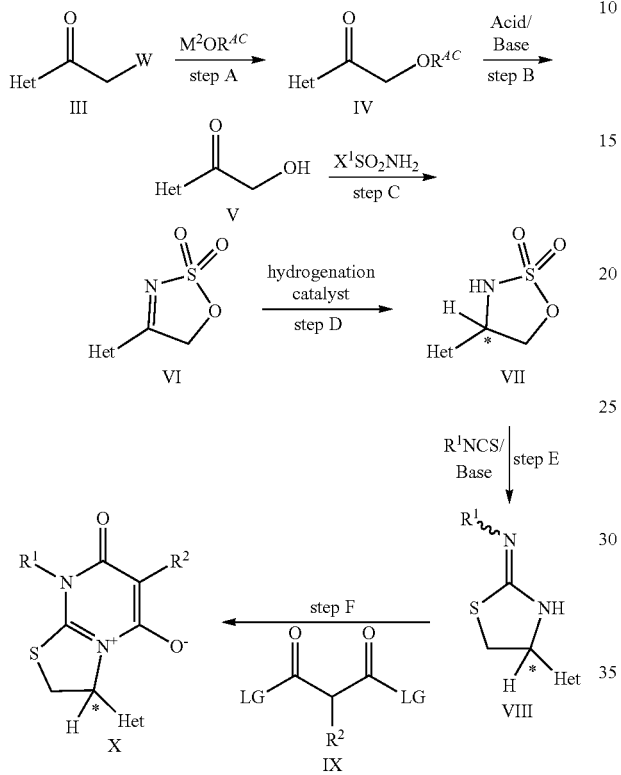

The present invention relates to a process for preparing S-containing pyrimidinium compound of formula X. The pyrimidinium compounds of formula X have insecticidal properties which is known from WO2014/167084. However, the process of preparing the optically active S-containing pyrimidinium compound of formula X is not described in the prior art. The present invention to prepare optically enriched S-containing pyrimidinium compound of formula X is based on asymmetric transfer hydrogenation of cyclic imine of formulae VI. Further, it is known from the literature that enantiomers can display different spectrum of pesticidal or insecticidal activities. It is also possible that while one specific enantiomer shows insecticidal activity, its counterpart may be completely inactive on insects. Thus, it has become a stringent requirement of any approval administration to use chiral compounds with pesticidal or insecticidal activity only in its respective active enantiomeric form. Thus, there is a need for a process to prepare the optically active compound of formula X with more than 90% enantiomeric excess and with a high yield via a short route.

This object is achieved by the processes described in detail hereinafter.

A first aspect of the present invention relates to a process for preparing S-containing pyrimidinium compound of formula X wherein

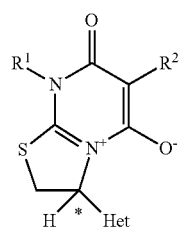

C* is an asymmetric carbon atom of S or R-configuration;
R$^1$ is $C_1$-$C_4$-alkyl, $C_3$-$C_6$-cycloalkyl, $C_2$-$C_4$-alkenyl, or —$CH_2$-phenyl, which groups are unsubstituted or substituted with halogen or $C_1$-$C_4$-alkyl;
R$^2$ is a 5- or 6-membered saturated, partially unsaturated or aromatic carbo- or heterocyclic ring, wherein the ring is unsubstituted or substituted with R$^{2a}$;
Het is selected from D-1, D-2, and D-3:

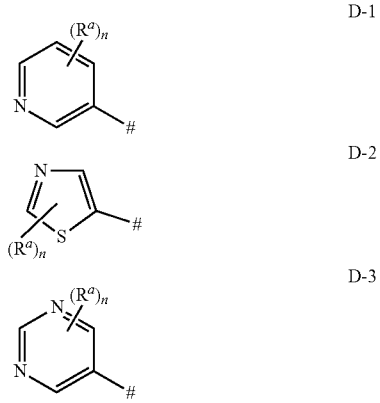

wherein
R$^a$ is each independently R$^a$ is halogen, $C_1$-$C_4$-haloalkyl, $C_1C_4$-alkoxy, $C_1$-$C_4$-alkylthio, or phenyl;
n is 0, 1 or 2; and
# denotes the bond in formula X;
R$^{2a}$ is halogen, $C_1$-$C_6$-haloalkyl, $C_1$-$C_6$-haloalkoxy, OR$^c$, C(=O)OR$^c$, C(=O)NR$^b$R$^c$, phenyl, or pyridyl, which is unsubstituted or substituted with halogen, $C_1$-$C_6$-haloalkyl or $C_1$-$C_6$-haloalkoxy;
R$^b$ is hydrogen, $C_1$-$C_6$-alkyl, $C_1$-$C_6$-haloalkyl, $C_1$-$C_6$-alkoxy, or $C_1$-$C_6$-haloalkoxy;
R$^c$ is hydrogen, $C_1$-$C_4$-alkyl, $C_1$-$C_4$-haloalkyl, or $C_1$-$C_6$ cycloalkyl;
  wherein two geminally bound groups R$^c$R$^b$ together with the atom to which they are bound, may form a 3- to 7-membered saturated, partially unsaturated or aromatic heterocyclic ring;
comprising at least the steps of:
(A) reacting a compound of formula III,

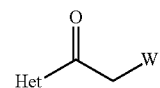

wherein
W is halogen, O-p-toluenesulfonyl, O-methanesulfonyl, or O-trifluoromethanesulfonyl;
Het is as defined in compound of formula X as above;
with $M^2OR^{AC}$ wherein $M^2$ is selected from lithium, sodium, potassium, aluminium, barium, cesium, calcium, and magnesium; $R^{AC}$ is $C(=O)C_1$-$C_4$-alkyl;
to obtain the compound of formula IV

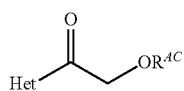

IV wherein Het and $R^{AC}$ are as defined herein;
(B) hydrolyzing the compound of formula IV as defined herein, in the presence of an acid or a base, to obtain a compound of formula V,

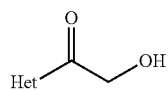

V wherein Het is as defined in compound of formula IV;
(C) reacting the compound of formula V with $X^2SO_2NH_2$ wherein $X^2$ is halogen, to obtain the compound of formula VI

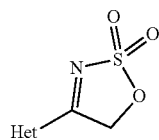

VI wherein Het is as defined in compound of formula V,
(D) hydrogenation of the compound of formula VI, in the presence of a hydrogenation catalyst $MXLn(\eta\text{-arene})_m$, wherein
M is a transition metal from group VIII to group XII of the periodic table;
X is an anion;
m is 0 or 1;
Ln is Ln1 or Ln2,
wherein
Ln1 is a chiral ligand of the formula Ln1

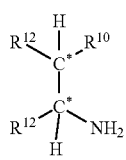

Ln1 wherein
C* is an asymmetric carbon atom of S or R-configuration;
$R^{10}$ is OH or NH—$SO_2$—$R^{11}$; wherein
$R^{11}$ is aryl unsubstituted or substituted with halogen, $C_1$-$C_{10}$-alkyl, $C_1$-$C_4$-alkoxy, $C_3$-$C_6$-cycloalkyl, $SO_3H$, or $SO_3Na$, or $C_1$-$C_{10}$-perfluoroalkyl, or $R^{13}R^{14}N$ wherein $R^{13}$ and $R^{14}$ independently represent $C_1$-$C_{10}$-alkyl unsubstituted or substituted with $C_6$-$C_{10}$-aryl, or $R^{13}$ and $R^{14}$ each independently represent a $C_6$-$C_1$-cycloalkyl;
$R^{12}$ independently represents aryl or $C_6$-$C_{10}$-cycloalkyl ring, wherein the ring is unsubstituted or substituted independently of each other with halogen, $C_1$-$C_{10}$-alkyl, $C_1$-$C_4$-alkoxy, $C_3$-$C_6$-cycloalkyl, $SO_3H$, or $SO_3Na$, or both $R^{12}$ are linked together to form a 3- to 6-membered carbocyclic ring or a 5- to 10-membered partially unsaturated carbocyclic ring;
Ln2 is a chiral phosphorous ligand;
and a hydrogen source selected from a)hydrogen, b) mixture of $N(R)_3$ wherein R is H or $C_1$-$C_6$-alkyl, and HCOOH, c) HCOONa or HCOOK, d) mixture of $C_1$-$C_8$-alcohol and t-BuOK, t-BuONa, or t-BuOLi, and e) combination of two or more from a) to d);
to obtain a compound of formula VII

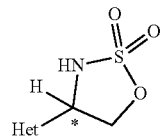

VII wherein
C* is an asymmetric carbon atom of S or R-configuration;
Het is as defined in compound of formula VI,
(E) reacting the compound of formula VII,

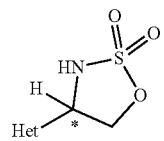

VII wherein
C* is an asymmetric carbon atom of S or R-configuration;
Het is as defined herein;
with $R^1NCS$, wherein $R^1$ is $C_1$-$C_4$-alkyl, $C_3$-$C_6$-cycloalkyl, $C_2$-$C_4$-alkenyl or —$CH_2$-phenyl, which groups unsubstituted or substituted by halogen or $C_1$-$C_4$-alkyl;
in the presence of a base,
to obtain a compound of formula VIII,

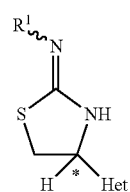

VIII wherein
C* and Het are as defined in the compound of formula VII;
$R^1$ is as defined herein,
(F) reacting the compound of formula VIII as defined herein, with a compound of formula IX

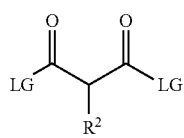

wherein,
LG is a leaving group selected from halogen, $OR^u$, and $SR^u$; wherein
$R^u$ is $C_1$-$C_6$-alkyl or aryl, which is unsubstituted or substituted with halogen;
$R^2$ is as defined in the compound of formula X;
to obtain the compound of formula X as defined herein.

The process of preparing the compound of formula X, optionally further comprises a process of preparing the compound of formula III by at least the steps of
(G) reacting a compound of formula I

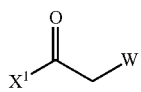

wherein W is as defined herein, and $X^1$ is halogen;
with $NH(R^Q)(R^P)$·HCl wherein $R^Q$ and $R^P$ independently are $C_1$-$C_6$-alkyl or $C_1$-$C_6$-alkoxy or $R^Q$ and $R^P$ are linked together to form a 5- to 7-membered carbocyclic or heterocyclic ring;
in the presence of a base,
to obtain the compound of formula II,

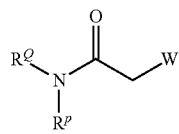

wherein $R^Q$, $R^P$ and W are as defined herein;
(H) reacting the Het as defined herein, with a compound of formula II as defined herein, in the presence of a $R^L MgX^1$ or $R^L Li$; wherein $R^L$ is $C_1$-$C_6$-alkyl; $X^1$ is halogen;
and a metal halide wherein the metal is lithium, sodium, potassium, or magnesium, to obtain the compound of formula III,

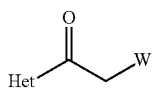

wherein Het and W are as defined herein.

The compound of formula III can also be prepared by analogy to the methods as described herein or methods known from WO 2014/167084 or other methods known in the literature. Starting materials used in the process are commercially available or can be prepared by methods known in the literature.

Further aspect of the present invention relates to a process of preparing the compound of formula X as defined herein, comprising one or more of the steps of (A), (B), (C), (D), (E), (F), (G), and (H) as described herein, preferably in the sequence (H)→(G)→(A)→(B)→(C)→(D)→(E)→(F) as described herein.

The compounds of formula VI can be used as versatile intermediate in preparation of optically enriched cyclic amine derivatives of formulae VII. Hence there is a need to develop a process for preparing the compound of formula VI. This object is achieved by providing the compound of formula VI and a process for preparing the compound of formula VI.

A further aspect of the present invention relates to a process of preparing a compound of formula VI as defined herein,

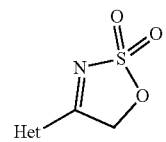

comprising,
reacting the compound of formula V as defined herein,

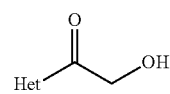

with $X^1SO_2NH_2$ wherein $X^1$ is a halogen, as described in the step (C) herein.

Further aspect of the present invention relates to a compound of formula VI or salts and N-oxides thereof.

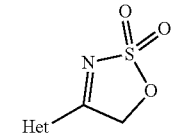

wherein Het is as defined herein.

Compounds of formula VII, particularly the optically enriched compounds of formula VII can be used as versatile intermediates for the preparation of pharmaceutical and agrochemical intermediates or active ingredients. Furthermore, the compounds of formula VII can be used in preparation of pesticides or N-containing heterocyclic moiety, for example compounds of formula VIII or the compounds of formula X which are known from WO 2014/167084 to be particularly useful for combating invertebrate pests. However, a process of preparing the optically enriched compound of formula VII, as defined herein, is not known.

Hence there is a need to develop a process for preparing the optically active compound of formula VII, more specifically a process for preparing the optically active compound of formula VII with an enantiomeric excess, preferably >70%, more preferably >85%, most preferably >95%. This object is achieved by providing the optically active compound of formula VII and a process for preparing the optically active compound of formula VII with an enantiomeric excess preferably >95%.

Further aspect of the present invention relates to a process of preparing a compound of formula VII as defined herein,

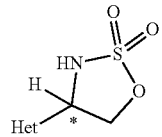
VII by hydrogenation of a compound of formula VI as defined herein,

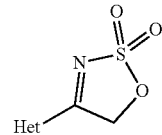
VI as described in the step (D) herein.

Further aspect of the present invention relates to an optically active compound of formula VII or salts and N-oxides thereof.

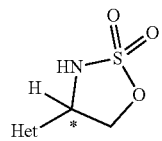
VII wherein C* and Het are as defined herein.

Further, the optically active amine compounds of formula VIII can be used as versatile intermediate compounds for the preparation of pesticides with amine derivative, or N containing heterocyclic moiety, for example the compounds of formula X which are known from WO 2014/167084 to be particularly useful for combating invertebrate pests. However, a process of preparing the optically active compound of formula VIII is not known.

Hence there is a need to develop a process for preparing the optically active compound of formula VIII, more specifically a process for preparing the optically active compound of formula VIII with an enantiomeric excess, preferably >80%, more preferably >95%.

This object is achieved by providing the optically active compound of formula VIII and a process for preparing the optically active compound of formula VIII with an enantiomeric excess preferably >95%.

Further aspect of the present invention relates to a process of preparing the compound of formula VIII as defined herein,

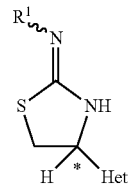
VIII comprising, reacting a compound of formula VII as defined in herein, with $R^1NCS$ wherein $R^1$ is as defined herein,

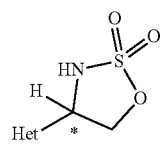
VII in the presence of a base, as described in the step (E) herein.

Further aspect of the present invention relates to an optically active compound of formula VIII or salts and N-oxides thereof.

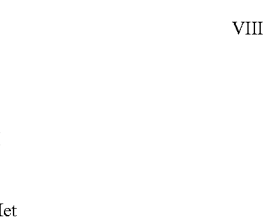
VIII wherein C*, Het and $R^1$ are as defined herein.

Further aspect of the present invention relates to a process of preparing the compound of formula X as defined herein, reacting the compound of formula VIII as defined herein, with a compound of formula IX as defined herein, as described in the step (F) herein.

The molecular structure of compound of formula X may exist in different isoelectronic formulae, each having the formal positive and negative charges on different atoms, as shown below.

The present invention extends to process of preparing all representative isoelectronic structures of compounds of formula X.

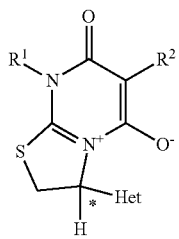
X

X 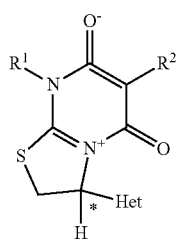

X 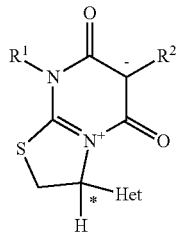

X 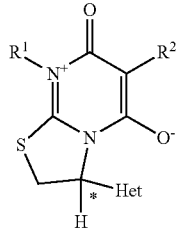

X 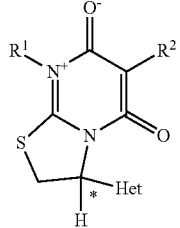

X 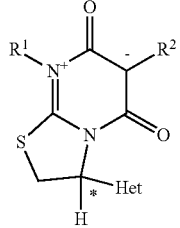

The "present invention", "invention" or "process of the present invention" refers to one or more of the steps (A), (B), (C), (D), (E), (F), (G), and (H), preferably to one or more of the steps (A), (B), (C), (D), (E), and (F). The "compounds of the present invention" or "compounds according to the invention", i.e. the compounds of formulae VI, VII, or VIII as defined herein, comprise the compound(s) as such as well as salts, tautomers or N-oxides thereof, if the formation of these derivatives is possible.

The term "stereoisomer(s)" encompasses both optical isomers, such as enantiomers or diastereomers, the latter existing due to more than one center of chirality in the molecule, as well as geometrical isomers (cis/trans isomers). The present invention or the compounds of present invention relates to every possible stereoisomer of the compounds of the invention, i.e. to single enantiomers or diastereomers, as well as to mixtures thereof.

The compounds according to the invention may be amorphous or may exist in one or more different crystalline states (polymorphs) which may have different macroscopic properties such as stability or show different biological properties such as activities. The present invention relates to amorphous and crystalline compounds according to the invention, mixtures of different crystalline states of the respective compounds according to the invention, as well as amorphous or crystalline salts thereof.

Salts of the compounds according to the invention can be formed in a customary manner, e.g. by reacting the compound with an acid of the anion in question if the compounds according to the invention have a basic functionality or by reacting acidic compounds according to the invention with a suitable base. Salts of the compounds according to the invention are preferably agriculturally and/or veterinary acceptable salts, preferably agriculturally acceptable salts.

The term "N-oxide" includes any compound of the present invention which has at least one tertiary nitrogen atom that is oxidized to an N-oxide moiety.

As used herein, the term "hydrogenation catalyst" covers homogeneous hydrogenation catalysts. It is known in the art that rhodium, ruthenium, iridium, platinum, palladium, iron or nickel form highly active catalysts. Preferred hydrogenation catalysts according to the invention are provided further below.

Anions of useful acid addition salts are primarily halides such as chloride, bromide, and fluoride; hydrogen sulfate, sulfate, dihydrogen phosphate, hydrogen phosphate, phosphate, nitrate, hydrogen carbonate, carbonate, hexafluorosilicate, hexafluorophosphate, benzoate, and the anions of $C_1$-$C_4$-alkanoic acids, preferably formate, acetate, propionate and butyrate. They can be formed by reacting the M or MLn with an acid of the corresponding anion, preferably of hydrochloric acid, hydrobromic acid, sulfuric acid, phosphoric acid or nitric acid.

The organic moieties groups mentioned in the above definitions of the variables are—like the term halogen—collective terms for individual listings of the individual group members. The prefix $C_n$-$C_m$ indicates in each case the possible number of carbon atoms in the group.

"Halogen" will be taken to mean flouro, chloro, bromo and iodo.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine.

The term "$CO_n$—$C_m$-alkyl" as used herein (and also in $C_n$-$C_m$-alkylamino, di-$C_n$-$C_m$-alkylamino, $C_n$-$C_m$-alkylaminocarbonyl, di-($C_n$-$C_m$-alkylamino)carbonyl, $C_n$-$C_m$-alkylthio, $CO_n$-$C_m$-alkylsulfinyl and $C_n$-$C_m$-alkylsulfonyl) refers to a branched or unbranched saturated hydrocarbon group having n to m, e.g. 1 to 10 carbon atoms, preferably 1 to 6 carbon atoms, for example methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, heptyl, octyl, 2-ethylhexyl, nonyl and decyl and their isomers. $C_1$-$C_4$-alkyl means for example methyl, ethyl, propyl, 1-methylethyl, butyl, 1-methylpropyl, 2-methylpropyl or 1,1-dimethylethyl.

The term "$C_n$-$C_m$-haloalkyl" as used herein (and also in $C_n$-$C_m$-haloalkylsulfinyl and $CO_n$—$C_m$-haloalkylsulfonyl) refers to a straight-chain or branched alkyl group having n to m carbon atoms, e.g. 1 to 10 in particular 1 to 6 carbon atoms (as mentioned above), where some or all of the hydrogen atoms in these groups may be replaced by halogen atoms as mentioned above, for example $C_1$-$C_4$-haloalkyl, such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and the like. The term $C_1$-$C_{10}$-haloalkyl in particular comprises $C_1$-$C_2$-fluoroalkyl, which is synonym with methyl or ethyl, wherein 1, 2, 3, 4 or 5 hydrogen atoms are substituted by fluorine atoms, such as fluoromethyl, difluoromethyl, trifluoromethyl, 1-fluoroethyl, 2-fluoroethyl, 2,2-difluoroethyl, 2,2,2-trifluoroethyl and pentafluoromethyl.

Similarly, "$C_n$-$C_m$-alkoxy" and "$C_n$-$C_m$-alkylthio" (or $C_n$-$C_m$-alkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen (or sulfur linkages, respectively) at any bond in the alkyl group. Examples include $C_1$-$C_4$-alkoxy such as methoxy, ethoxy, propoxy, isopropoxy, butoxy, sec-butoxy, isobutoxy and tert-butoxy, further $C_1$-$C_4$-alkylthio such as methylthio, ethylthio, propylthio, isopropylthio, and n-butylthio.

Accordingly, the terms "$C_n$-$C_m$-haloalkoxy" and "$C_n$-$C_m$-haloalkylthio" (or $C_n$-$C_m$-haloalkylsulfenyl, respectively) refer to straight-chain or branched alkyl groups having n to m carbon atoms, e.g. 1 to 10, in particular 1 to 6 or 1 to 4 carbon atoms (as mentioned above) bonded through oxygen or sulfur linkages, respectively, at any bond in the alkyl group, where some or all of the hydrogen atoms in these groups may be replaced by halogen atoms as mentioned above, for example $C_1$-$C_2$-haloalkoxy, such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy and pentafluoroethoxy, further $C_1$-$C_2$-haloalkylthio, such as chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoroethylthio, 2,2-dichloro-2-fluoroethylthio, 2,2,2-trichloroethylthio and pentafluoroethylthio and the like. Similarly, the terms $C_1$-$C_2$-fluoroalkoxy and $C_1$-$C_2$-fluoroalkylthio refer to $C_1$-$C_2$-fluoroalkyl which is bound to the remainder of the molecule via an oxygen atom or a sulfur atom, respectively.

The term "$C_2$-$C_m$-alkenyl" as used herein intends a branched or unbranched unsaturated hydrocarbon group having 2 to m, e.g. 2 to 10 or 2 to 6 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

The term "$C_2$-$C_m$-alkynyl" as used herein refers to a branched or unbranched unsaturated hydrocarbon group having 2 to m, e.g. 2 to 10 or 2 to 6 carbon atoms and containing at least one triple bond, such as ethynyl, propynyl, 1-butynyl, 2-butynyl, and the like.

The suffix "-carbonyl" in a group or "C(=O)" denotes in each case that the group is bound to the remainder of the molecule via a carbonyl C=O group. This is the case e.g. in alkylcarbonyl, haloalkylcarbonyl, aminocarbonyl, alkylaminocarbonyl, dialkylaminocarbonyl, alkoxycarbonyl, haloalkoxycarbonyl.

The term "aryl" as used herein refers to a mono-, bi- or tricyclic aromatic hydrocarbon radical such as phenyl or naphthyl, in particular phenyl (also referred as to $C_6H_5$ as substituent).

The term "ring system" denotes two or more directly connected rings.

The term "$C_3$-$C_m$-cycloalkyl" as used herein refers to a monocyclic ring of 3- to m-membered saturated cycloaliphatic radicals, e.g. cyclopropyl, cyclobutyl, cyclopentyl, cyclohexyl, cycloheptyl, cyclooctyl and cyclodecyl.

The term "5- to 10-membered partially unsaturated carbocyclic ring" as used herein refers to partially unsaturated monocyclic or bicyclic ring containing 5 to 10 carbon atoms, for example indane.

The term "3- to 7-membered carbocyclic ring" as used herein refers to cyclopropane, cyclobutane, cyclopentane, cyclohexane and cycloheptane rings.

The term "heterocyclic ring" refers "3-, 4-, 5-, 6- or 7-membered saturated, partially unsaturated or aromatic heterocyclic ring which may contain 1, 2, 3 or 4 heteroatoms" or "containing heteroatom groups", wherein those heteroatom(s) (group(s)) are selected from N (N-substituted groups), O and S (S-substituted groups) as used herein refers to monocyclic radicals, the monocyclic radicals being saturated, partially unsaturated or aromatic (completely unsaturated). The heterocyclic radical may be attached to the remainder of the molecule via a carbon ring member or via a nitrogen ring member.

Examples of 3-, 4-, 5-, 6- or 7-membered saturated heterocyclyl or heterocyclic rings include: oxiranyl, aziridinyl, azetidinyl, 2-tetrahydrofuranyl, 3-tetrahydrofuranyl, 2-tetrahydrothienyl, 3-tetrahydrothienyl, 2-pyrrolidinyl, 3-pyrrolidinyl, 3-pyrazolidinyl, 4-pyrazolidinyl, 5-pyrazolidinyl, 2-imidazolidinyl, 4-imidazolidinyl, 2-oxazolidinyl, 4-oxazolidinyl, 5-oxazolidinyl, 3-isoxazolidinyl, 4-isoxazolidinyl, 5-isoxazolidinyl, 2-thiazolidinyl, 4-thiazolidinyl, 5-thiazolidinyl, 3-isothiazolidinyl, 4-isothiazolidinyl, 5-isothiazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, -1,3,4-oxadiazolidin-2-yl, 1,3,4-thiadiazolidin-2-yl, 1,3,4-triazolidin-2-yl, 2-tetrahydropyranyl, 4-tetrahydropyranyl, 1,3-dioxan-5-yl, 1,4-dioxan-2-yl, 2-piperidinyl, 3-piperidinyl, 4-piperidinyl, 3-hexahydropyridazinyl, 4-hexahydropyridazinyl, 2-hexahydropyrimidinyl, 4-hexahydropyrimidinyl, 5-hexahydropyrimidinyl, 2-piperazinyl, 1,3,5-hexahydrotriazin-2-yl and 1,2,4-hexahydrotriazin-3-yl, 2-morpholinyl, 3-morpholinyl, 2-thiomorpholinyl, 3-thiomorpholinyl, 1-oxothiomorpholin-2-yl, 1-oxothiomorpholin-3-yl, 1,1-dioxothiomorpholin-2-yl, 1,1-dioxothiomorpholin-3-yl, hexahydroazepin-1-, -2-, -3- or -4-yl, hexahydrooxepinyl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like.

Examples of 3-, 4-, 5-, 6- or 7-membered partially unsaturated heterocyclyl or heterocyclic rings include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin 3 yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3 dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7 tetrahydro [1H]azepin-1-, -2-, -3-, -4-, -5-, -6- or -7-yl, 2,3,6,7 tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7 tetrahydro[1H]oxepin-2-, -3-, -4-, -5-, -6- or -7-yl, 2,3,6,7 tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

Examples of 5- or 6-membered aromatic heterocyclic (hetaryl) or heteroaromatic rings are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

The term "substituted" if not specified otherwise refers to substituted with 1, 2 or maximum possible number of substituents. If substituents as defined in compounds of formula I are more than one then they are independently from each other are same or different if not mentioned otherwise.

Meaning of the terms that are not defined herein are generally known to a person skilled in the art or in the literature.

Preferred embodiments of the present invention are described below.

Preferences

In one embodiment, $R^1$ $C_1$-$C_4$-alkyl, $C_3$-$C_6$-cycloalkyl, or $C_2$-$C_4$-alkenyl, which is unsubstituted, or substituted with halogen.

In another embodiment, $R^1$ is $C_1$-$C_4$-alkyl.

In another embodiment, $R^1$ is methyl or ethyl.

In another embodiment, $R^1$ is methyl.

In one embodiment, $R^2$ is phenyl, pyridinyl or thiophenyl, which are unsubstituted or substituted with $R^{2a}$.

In another embodiment, $R^2$ is phenyl, which is unsubstituted or substituted with $R^{2a}$, wherein $R^{2a}$ is halogen, $C_1$-$C_6$-haloalkyl, $C_1$-$C_6$-haloalkoxy, OR, C(=O)OR, C(=O)NR$^b$R$^c$, phenyl, or pyridyl, which may be substituted by halogen, $C_1$-$C_6$-haloalkyl or $C_1$-$C_6$-haloalkoxy.

In another embodiment, $R^2$ is phenyl, which is unsubstituted or substituted with halogen, $C_1$-$C_4$-alkyl or $C_1$-$C_3$-haloalkyl.

In another embodiment, $R^2$ is phenyl, which is unsubstituted or substituted with trifluoromethyl or halogen, preferably chloro;

In another embodiment, $R^2$ is phenyl, 3,5-dichlorophenyl, 3-trifluoromethylphenyl.

In another embodiment, $R^2$ is phenyl.

In another embodiment, $R^2$ is 3,5-dichlorophenyl.

In another embodiment, $R^2$ is 3-trifluoromethylphenyl.

In an embodiment, $R^a$ is halogen, $C_1$-$C_4$-haloalkyl, $C_1$C_4$-alkoxy, $C_1$-$C_4$-alkylthio, or phenyl.

In a more preferred embodiment, $R^a$ is halogen or $C_1$-$C_4$-haloalkyl.

In a most preferred embodiment, $R^a$ is halogen, preferably Cl.

In another preferred embodiment, $R^a$ is phenyl.

In an embodiment, n is 0.

In another embodiment, n is 1.

In another embodiment, n is 2.

In one embodiment of the invention, Het is D-2;

In one embodiment of the invention, Het is selected from D-1, D-2, and D-3, wherein
$R^a$ is chloro,
n is 1.

In another embodiment, Het is D-1a, D-2a, and D-3a:

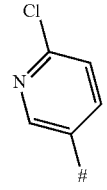

D-1a

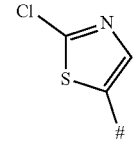

D-2a

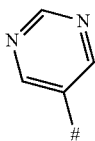

D-3a

In another embodiment, Het is D-1a.
In another embodiment, Het is D-2a.
In another embodiment, Het is D-3a.
In one embodiment of the invention, the compound of formula X is one of the following compounds X-1 to X-6:

| Compound No | $R^1$ | $R^2$ | Het |
|---|---|---|---|
| X-1 | $CH_3$ | Ph | D-1a |
| X-2 | $CH_3$ | Ph | D-2a |
| X-3 | $CH_3$ | Ph | D-3a |
| X-4 | $CH_3$ | 3-(trifluoromethyl)phenyl | D-2a |
| X-5 | $CH_3$ | 3,5-dichlorophenyl | D-2a |
| X-6 | $CH_2CH_3$ | Ph | D-2a |

In one embodiment of the invention, the compound of formula X is the compound X-1.

In another embodiment of the invention, the compound of formula X is the compound X-2.

In another embodiment of the invention, the compound of formula X is the compound X-3.

In another embodiment of the invention, the compound of formula X is the compound X-4.

In another embodiment of the invention, the compound of formula X is the compound X-5.

In another embodiment of the invention, the compound of formula X is the compound X-6.

In an embodiment, W is halogen, hydroxy, O-p-toluenesulfonyl, O-methanesulfonyl, or O-trifluoromethanesulfonyl.

In a preferred embodiment, W is halogen, O-p-toluenesulfonyl, O-methanesulfonyl, or O-trifluoromethanesulfonyl; In a more preferred embodiment, W is halogen.

In another more preferred embodiment, W is hydroxy.

Preferred embodiments regarding the steps (A), (B), (C), (D), (E), and (F) of the invention are described hereinafter.

In general, the reaction steps performed in the steps (A), (B), (C), (D), (E), and (F) as described in detail hereinafter are performed in reaction vessels customary for such reactions, the reactions being carried out in a continuous, semicontinuous or batch wise manner.

In general, the particular reactions will be carried out under atmospheric pressure. The reactions may, however, also be carried out under reduced pressure.

In general, products obtained by any of the reaction steps (D), (E), and (F) results in enantiomeric excess. However, enantiomeric excess can be further increased during isolation, purification for example crystallization of an enantiomer, as well as during or after use of the product.

The temperatures and the duration times of the reactions may be varied in broad ranges, which the person skilled in the art knows from analogous reactions. The temperatures often depend on the reflux temperature of the solvents. Other reactions are preferably performed at room temperature, i.e. at about 25° C., or under ice cooling, i.e. at about 0° C. The end of the reaction can be monitored by methods known to a person skilled in the art, e.g. thin layer chromatography or HPLC.

If not otherwise indicated, the molar ratios of the reactants, which are used in the reactions, are in the range of from 0.2:1 to 1:0.2, preferably from 0.5:1 to 1:0.5, more preferably from 0.8:1 to 1:0.8. Preferably, equimolar amounts are used.

If not otherwise indicated, the reactants can in principle be contacted with one another in any desired sequence.

The person skilled in the art knows when the reactants or reagents are moisture sensitive, so that the reaction should be carried out under protective gases such as under a nitrogen atmosphere, and dried solvents should be used.

The person skilled in the art also knows the best work-up of the reaction mixture after the end of the reaction.

In the following, preferred embodiments regarding step (A) of the invention are provided. It is to be understood that the preferred embodiments mentioned above and those still to be illustrated below of step (A) of the invention are to be understood as preferred alone or in combination with each other.

In an embodiment, $M^2$ is selected from lithium, sodium, potassium, aluminium, barium, caesium, calcium, and magnesium;

In a preferred embodiment, $M^2$ is lithium;
In another preferred embodiment, $M^2$ is sodium;
In another preferred embodiment, $M^2$ is potassium;
In another preferred embodiment, $M^2$ is aluminium;
In another preferred embodiment, $M^2$ is barium;
In another preferred embodiment, $M^2$ is cesium;
In another preferred embodiment, $M^2$ is calcium;
In another preferred embodiment, $M^2$ is magnesium;
In an embodiment, $R^{4C}$ is (=O)$C_1$-$C_4$-alkyl;
In another embodiment, $R^{4C}$ is (=O)$C_1$-$C_3$-alkyl; preferably C(=O)methyl, C(=O)ethyl, C(=O)n-propyl, or C(=O)isopropyl; more preferably C(=O)methyl; In an embodiment, the reaction temperature in step (A) is kept within a range of from 0 to 120° C., preferably in the range of from 20 to 100° C., more preferably in the range of from 20° to 60° C.

In an embodiment the step (A) is carried out in the absence of a solvent.

In another embodiment the step (A) is carried out in a solvent.

Suitable solvents include water and aliphatic hydrocarbons such as pentane, hexane, cyclohexane and petroleum ether; aromatic hydrocarbons such as toluene, o-, m- and p-xylene; halogenated hydrocarbons such as methylene chloride, chloroform and chlorobenzene; alcohols such as methanol, ethanol, n-propanol, isopropanol, n-butanol and tert-butanol; $C_2$-$C_4$-alkandiols, such as ethylene glycol or propylene glycol; ether alkanols such as diethylene glycol; carboxylic esters such as ethyl acetate; N-methylpyrrolidone; dimethylformamide; dimethyl acetamide; and ethers including open-chained and cyclic ethers, especially diethyl ether, methyl-tertbutyl-ether (MTBE), 2-methoxy-2-methylbutane, cyclopentylmethylether, 1,4-dioxane, tetrahydrofuran, and 2-methyltetrahydrofuran, in particular tetrahydrofuran, MTBE, and 2-methyltetrahydrofuran. Mixtures of said solvents can also be used.

In a preferred embodiment, solvent is selected from water, $C_2$-$C_6$-alkandiols, $C_1$-$C_6$-haloalkanes, halobenzene, carboxylic esters, N-methylpyrrolidone; dimethylformamide; dimethyl acetamide and ethers including open-chained and cyclic ethers, or mixture of the two or more thereof.

In another preferred embodiment, solvent is selected from dimethylformamide, tetrahydrofuran, 2-methyltetrahydrofuran, N-methylpyrrolidone, dimethyl acetamide or mixture of the two or more thereof.

In an embodiment, the volume ratio of the compound of formula III to solvent is in the range of 1:30 to 1:0.

In another embodiment, the volume ratio of the compound of formula III to solvent is in the range of 1:20 to 1:10.

In a preferred embodiment, the volume ratio of the compound of formula III to solvent is in the range of 1:10 to 1:0.

In the following, preferred embodiments regarding step (B) of the invention are provided. It is to be understood that the preferred embodiments mentioned above and those still to be illustrated below of step (B) of the invention are to be understood as preferred alone or in combination with each other.

In an embodiment, the step (B) is carried out in the presence of an acid; In an embodiment, suitable acids are in general Inorganic acids such as hydrofluoric acid, hydrochloric acid, hydrobromic acid, hydroiodic acid, sulphuric acid, phosphoric acid, perchloric acid, or mixture of one or more thereof.

In a preferred embodiment, the acid is hydrochloric acid, sulphuric acid, phosphoric acid, hydroiodic acid, or mixture of one or more thereof.

In another embodiment, suitable acids are Lewis acids, such as boron tri fluoride, aluminium tri chloride, iron (III) chloride, tin (IV) chloride, titanium (IV) chloride and zinc (II) chloride.

In another embodiment, suitable acids are in general organic acids such as formic acid, $C_1$-$C_8$-alkyl-$(COOH)_y$, or $C_1$-$C_8$-haloalkyl-$(COOH)_y$, wherein y is 1 or 2; $CH_3SO_3H$, citric acid, oxalic acid, p-toluenesulfonic acid acetic acid, propionic acid, oxalic acid, toluene sulfonic acid, benzene sulfonic acid, camphor sulfonic acid, citric acid, and trifluoro acetic acid, or mixture of one or more thereof.

In a preferred embodiment, the acid is $C_1$-$C_8$-alkyl-$(COOH)_y$, $C_1$-$C_8$-haloalkyl-$(COOH)_y$, wherein y is 1 or 2, $CH_3SO_3H$, citric acid, oxalic acid, p-toluenesulfonic acid, or mixture of two or more thereof.

In another embodiment, the acid in step (B) is selected from hydrochloric acid, sulphuric acid, phosphoric acid, polyphosphoric acid, hydroiodic acid, $C_1$-$C_8$-alkyl-$(COOH)_y$, $C_1$-$C_8$-haloalkyl$(COOH)_y$, $CH_3SO_3H$, citric acid, oxalic acid, p-toluenesulfonic acid, or mixture of two or more thereof; wherein y is 1 or 2.

In a particularly preferred embodiment, the acid in step (B) is hydrochloric acid.

The acids are generally employed in equimolar amounts; however, they can also be used in catalytic amounts, in excess or, if appropriate, as solvent.

In another embodiment, the step (B) is carried out in the presence of an acid and a buffer.

Buffers include aqueous and non-aqueous buffers, and are preferably non-aqueous buffers.

Preferred buffers include buffers based on acetate, phosphate or formate, e.g. sodium acetate, potassium hydrogen phosphate, potassium dihydrogen phosphate, or ammonium formate.

In an embodiment, the step (B) is carried out in the presence of a base; Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide, and magnesium oxide, alkali metal and alkaline earth metal carbonates, such as lithium carbonate, potassium carbonate and calcium carbonate, and also In one particularly preferred embodiment, the base is selected from alkali metal and alkaline earth metal hydroxides, in particular from the group consisting of lithium hydroxide, sodium hydroxide, magnesium hydroxide, potassium hydroxide, and calcium hydroxide.

In another particularly preferred embodiment, the base is selected from alkali metal and alkaline earth metal oxides, in particular from the group consisting of lithium oxide, sodium oxide, calcium oxide, and magnesium oxide.

The bases are generally employed in equimolar amounts; however, they can also be used in catalytic amounts or in excess.

In an embodiment, the reaction temperature hydrolysis in step (B) is kept within a range of from 0 to 120° C., preferably in the range of from 20 to 100° C., more preferably in the range of from 20° to 60° C.

In an embodiment the hydrolysis in step (B) is carried out in the absence of a solvent.

In another embodiment the hydrolysis in step (B) is carried out in a solvent.

Suitable solvents include water and aliphatic hydrocarbons such as pentane, hexane, cyclohexane and petroleum ether; aromatic hydrocarbons such as toluene, o-, m- and p-xylene; halogenated hydrocarbons such as methylene chloride, chloroform and chlorobenzene; alcohols such as methanol, ethanol, n-propanol, isopropanol, n-butanol and tert-butanol; $C_2$-$C_4$-alkandiols, such as ethylene glycol or propylene glycol; ether alkanols such as diethylene glycol; carboxylic esters such as ethyl acetate; N-methylpyrrolidone; dimethylformamide; and ethers including open-chained and cyclic ethers, especially diethyl ether, methyl-tert-butyl-ether (MTBE), 2-methoxy-2-methylbutane, cyclopentylmethylether, 1,4-dioxane, tetrahydrofuran, and 2-methyltetrahydrofuran, in particular tetrahydrofuran, MTBE, and 2-methyltetrahydrofuran. Mixtures of said solvents can also be used.

In another embodiment, the solvent is selected from $C_1$-$C_6$-alcohol, water, $C_2$-$C_6$-alkandiols, carboxylic esters, N-methylpyrrolidone, dimethylformamide, and ethers including open-chained and cyclic ethers, or mixture of the two or more thereof.

In another embodiment, the solvent is selected from water, dimethylformamide, N-methylpyrrolidone, methyl-tert-butyl-ether, methanol, ethanol, isopropanol, or mixture of two or more thereof.

Preferred solvents are protic solvents, preferably alcohols selected from the group consisting of such as methanol, ethanol, n-propanol, isopropanol, n-butanol and tert-butanol.

In a preferred embodiment, the solvent is a $C_1$-$C_4$-alcohol, in particular methanol.

In an embodiment, the volume ratio of the compound of formula VI to solvent is in the range of 1:30 to 1:0.

In another embodiment, the volume ratio of the compound of formula VI to solvent is in the range of 1:20 to 1:10.

In a preferred embodiment, the volume ratio of the compound of formula VI to solvent is in the range of 1:10 to 1:0.

In the following, preferred embodiments regarding step (C) of the invention are provided. It is to be understood that the preferred embodiments mentioned above and those still to be illustrated below of step (C) of the invention are to be understood as preferred alone or in combination with each other.

In an embodiment, $X^1$ is halogen selected from Cl, Br, I, and F;

In a preferred embodiment, $X^1$ is Cl;

In another preferred embodiment, $X^1$ is Br;

In another preferred embodiment, $X^1$ is I;

In another preferred embodiment, $X^1$ is F;

In an embodiment, the step (C) is carried out in the presence of an acid;

In an embodiment, suitable acids are in general Inorganic acids such as hydrofluoric acid, hydrochloric acid, hydrobromic acid, hydroiodic acid, sulphuric acid, phosphoric acid, perchloric acid, or mixture of one or more thereof.

In a preferred embodiment, the acid is hydrochloric acid, sulphuric acid, phosphoric acid, hydroiodic acid, or mixture of one or more thereof.

In another embodiment, suitable acids are Lewis acids, such as boron tri fluoride, aluminium tri chloride, iron (III) chloride, tin (IV) chloride, titanium (IV) chloride and zinc (II) chloride.

In another embodiment, suitable acids are in general organic acids such as formic acid, $C_1$-$C_8$-alkyl-$(COOH)_y$, or $C_1$-$C_8$-haloalkyl-$(COOH)_y$, wherein y is 1 or 2; $CH_3SO_3H$, citric acid, oxalic acid, p-toluenesulfonic acid acetic acid, propionic acid, oxalic acid, toluene sulfonic acid, benzene sulfonic acid, camphor sulfonic acid, citric acid, and trifluoro acetic acid, or mixture of one or more thereof.

In a preferred embodiment, the acid is $C_1$-$C_8$-alkyl-$(COOH)_y$, $C_1$-$C_8$-haloalkyl-$(COOH)_y$, wherein y is 1 or 2, $CH_3SO_3H$, citric acid, oxalic acid, p-toluenesulfonic acid, or mixture of two or more thereof.

In another embodiment, the acid in step (C) is selected from hydrochloric acid, sulphuric acid, phosphoric acid, polyphosphoric acid, hydroiodic acid, $C_1$-$C_5$-alkyl-$(COOH)_y$, $C_1$-$C_5$-haloalkyl$(COOH)_y$, $CH_3SO_3H$, citric acid, oxalic acid, p-toluenesulfonic acid, or mixture of two or more thereof; wherein y is 1 or 2.

In a particularly preferred embodiment, the acid in step (C) is p-toluenesulfonic acid.

The acids are generally employed in equimolar amounts; however, they can also be used in catalytic amounts, in excess or, if appropriate, as solvent.

In another embodiment, the step (C) is carried out in the presence of an acid and a buffer.

Buffers include aqueous and non-aqueous buffers, and are preferably non-aqueous buffers.

Preferred buffers include buffers based on acetate, phosphate or formate, e.g. sodium acetate, potassium hydrogen phosphate, potassium dihydrogen phosphate, or ammonium formate.

In an embodiment, the reaction temperature in step (C) is kept within a range of from 0 to 150° C., preferably in the range of from 20 to 120° C., more preferably in the range of from 30° to 100° C.

In an embodiment the hydrolysis in step (C) is carried out in the absence of a solvent.

In another embodiment the hydrolysis in step (C) is carried out in a solvent.

Suitable solvents include water and aliphatic hydrocarbons such as pentane, hexane, cyclohexane and petroleum ether; aromatic hydrocarbons such as toluene, chlorobenzene, o-, m- and p-xylene; halogenated hydrocarbons such as methylene chloride, chloroform and chlorobenzene; alcohols such as methanol, ethanol, n-propanol, isopropanol, n-butanol and tert-butanol; $C_2$-$C_4$-alkandiols, such as ethylene glycol or propylene glycol; ether alkanols such as diethylene glycol; carboxylic esters such as ethyl acetate; N-methylpyrrolidone; dimethylformamide; and ethers including open-chained and cyclic ethers, especially diethyl ether, methyl-tert-butyl-ether (MTBE), 2-methoxy-2-methylbutane, cyclopentylmethylether, 1,4-dioxane, tetrahydrofuran, and 2-methyltetrahydrofuran, in particular tetrahydrofuran, MTBE, and 2-methyltetrahydrofuran. Mixtures of said solvents can also be used.

In another embodiment, the solvent is selected from $C_1$-$C_6$-alcohol, water, $C_2$-$C_6$-alkandiols, carboxylic esters, N-methylpyrrolidone, dimethylformamide, and ethers including open-chained and cyclic ethers, or mixture of the two or more thereof.

In another embodiment, the solvent is selected from water, dimethylformamide, N-methylpyrrolidone, methyl-tert-butyl-ether, methanol, ethanol, isopropanol, or mixture of two or more thereof.

Preferred solvents are aliphatic hydrocarbons such as pentane, hexane, cyclohexane and petroleum ether; aromatic hydrocarbons such as toluene, chlorobenzene, o-, m- and p-xylene.

In a particularly preferred embodiment, the solvent is toluene.

In an embodiment, the volume ratio of the compound of formula V to solvent is in the range of 1:30 to 1:0.

In another embodiment, the volume ratio of the compound of formula V to solvent is in the range of 1:20 to 1:10.

In a preferred embodiment, the volume ratio of the compound of formula V to solvent is in the range of 1:10 to 1:0.

In the following, preferred embodiments regarding step (D) of the invention are provided. It is to be understood that the preferred embodiments mentioned above and those still to be illustrated below of step (D) of the invention are to be understood as preferred alone or in combination with each other.

In one embodiment, the hydrogen source selected from b) mixture of $N(R)_3$, wherein R is H or $C_1$-$C_6$-alkyl, and HCOOH, c) HCOONa, and d) mixture of isopropyl alcohol, and t-BuOK or t-BuONa, or t-BuOLi;

In one embodiment, the hydrogen source is a mixture of $N(R)_3$ and HCOOH.

In an embodiment, R is H;

In another embodiment, R is $C_1$-$C_6$-alkyl

In another embodiment, R is $C_1$-$C_4$-alkyl such as methyl, ethyl, isopropyl, n-propyl, ter-butyl.

In a preferred embodiment, R is H, ethyl, isopropyl, or ter-butyl.

In a more preferred embodiment, R is H or ethyl.

In a most preferred embodiment R is ethyl.

In an embodiment, volume ratio of $N(R)_3$ to HCOOH in the range of 1:2 to 1:10.

In a preferred embodiment, volume ratio of $N(R)_3$ to HCOOH is in the range of 1:1 to 1:4.

In more preferred embodiment, volume ratio of $N(R)_3$ to HCOOH is in the range of 1:1 to 1:3.

In another embodiment, the hydrogen source is HCOONa.

In another embodiment, the hydrogen source is HCOOK.

In another embodiment, the hydrogen source is mixture of isopropyl alcohol, and t-BuOK.

In another embodiment, the hydrogen source is mixture of isopropyl alcohol, and t-BuONa.

In an embodiment, m is 0;

In an embodiment, m is 1;

In an embodiment, the hydrogenation catalyst is MXLn($\eta$-arene)$_m$ wherein m is 1 $\eta$-arene is aryl ring which is unsubstituted or substituted with $C_1$-$C_4$-alkyl.

In an embodiment, the hydrogenation catalyst is MXLn($\eta$-arene)$_m$ wherein m is 1 and $\eta$-arene is selected from benzene, p-cymene, mesitylene, 2,4,6-triethylbenzene, hexamethylbenzene, anisole, 1,5-cyclooctadiene, cyclopentadienyl (Cp), norbornadiene, and pentamethylcyclopentadienyl (Cp*).

In an embodiment, the hydrogenation catalyst is MXLn($\eta$-arene)$_m$ wherein m is 1 and $\eta$-arene is selected from benzene, p-cymene, mesitylene, 2,4,6-triethylbenzene, hexamethylbenzene, anisole, 1,5-cyclooctadiene, cyclopentadienyl (Cp), and pentamethylcyclopentadienyl (Cp*).

In another embodiment, the hydrogenation catalyst is MXLn($\eta$-arene)$_m$ wherein m is 1 and $\eta$-arene is selected from cyclopentadienyl (Cp), and pentamethylcyclopentadienyl (Cp*).

In another embodiment, the hydrogenation catalyst is MXLn($\eta$-arene)$_m$ wherein m is 1 and $\eta$-arene is selected from cyclopentadienyl (Cp).

In another embodiment, the hydrogenation catalyst is MXLn($\eta$-arene)$_m$ wherein m is 1 and $\eta$-arene is pentamethylcyclopentadienyl (Cp*).

In another embodiment, the hydrogenation catalyst is MXLn($\eta$-arene)$_m$ wherein m is 1 and $\eta$-arene is selected from benzene, p-cymene, mesitylene, 2,4,6-triethylbenzene, hexamethylbenzene, anisole, and 1,5-cyclooctadiene.

In an embodiment, X is an anion formed by reacting the M or MLn with an acid of the corresponding anion, preferably of hydrochloric acid, hydrobromic acid, hydroiodic acid, tetrafluoroboric acid, or hexafluorophosphoric acid.

In another embodiment, X is selected from halides, hexafluorosilicate, hexafluorophosphate, benzoate, sulfonate and the anions of $C_1$-$C_6$-alkanoic acids, preferably formate, acetate, propionate and butyrate.

In another embodiment, X is halide selected from chloride, bromide, and iodide.

In another embodiment, X is chloride or bromide.

In another embodiment, X is chloride.

In another embodiment, X is tetrafluoroborate.

In another embodiment, Ln is Ln1 wherein $R^{10}$ is NH—$SO_2$—$R^{11}$ and wherein $R^{12}$ and $R^{11}$ independently are unsubstituted or substituted aryl.

In another embodiment, Ln is Ln1 wherein $R^{10}$ is NH—$S_2$—$R^{11}$ and wherein $R^{12}$ and $R^{11}$ independently are substituted aryl.

In another embodiment, Ln is Ln1 wherein $R^{10}$ is NH—$S_2$—$R^{11}$ and wherein $R^{12}$ and $R^{11}$ independently are unsubstituted aryl.

In another embodiment, Ln is Ln1 wherein $R^{10}$ is NH—$S_2$—$R^{11}$ and wherein $R^{11}$ is substituted aryl and $R^{12}$ is $C_6$-$C_{10}$-cycloalkyl.

In another embodiment, Ln is Ln1 and wherein $R^{10}$ is NH—$SO_2$—$R^{11}$; and wherein $R^{11}$ is substituted aryl and $R^{12}$ is unsubstituted aryl.

In another embodiment, Ln is Ln1 and wherein $R^{10}$ is NH—$S_2$—$R^{11}$; and wherein $R^{11}$ is unsubstituted aryl and $R^{12}$ is substituted aryl.

In another embodiment, Ln is Ln1 wherein $R^{10}$ is NH—$SO_2$—$R^{11}$ and wherein $R^{11}$ is unsubstituted or substituted aryl and both $R^{12}$ are linked together to form a 3- to 6-membered carbocyclic ring or a 5- to 10-membered partially unsaturated carbocyclic ring.

In another embodiment, MXLn($\eta$-arene)$_m$ is MXLn1($\eta$-arene)$_m$ and wherein $R^{10}$ is NH—$SO_2$—$R^{11}$; and $R^{12}$ and $R^{11}$ independently are phenyl which are unsubstituted or substituted with 1 or 2 substituents selected from halogen, $C_1$-$C_4$-alkyl, $C_1$-$C_4$-alkoxy, $C_3$-$C_6$-cycloalkyl, $SO_3H$, and $SO_3Na$.

In another embodiment, MXLn($\eta$-arene)$_m$ is MXLn1($\eta$-arene)$_m$ and wherein X is halide; $R^{12}$ independently is phenyl, 2-methylphenyl, 3-methylphenyl, 4-methylphenyl or 4-methoxyphenyl; $R^{10}$ is NH—$SO_2$—$R^{11}$ and —$SO_2$—$R^{11}$ is p-toluenesulfonyl, methanesulfonyl, 4-benzenesulfonyl, 4-trifluoromethylphenyl-sulfonyl or pentafluorophenylsulfonyl.

In another embodiment, Ln is Ln1 wherein $R^{10}$ is OH and $R^{12}$ is unsubstituted or substituted aryl.

In another embodiment, Ln is Ln1 wherein $R^{10}$ is OH and $R^{12}$ is substituted aryl.

In another embodiment, Ln is Ln1 wherein $R^{10}$ is OH and $R^{12}$ is unsubstituted aryl.

In another embodiment, Ln is Ln1 wherein $R^{10}$ is OH and $R^{12}$ is $C_6$-$C_{10}$-cycloalkyl.

In another embodiment, Ln is Ln1 wherein $R^{10}$ is OH and both $R^{12}$ are linked together to form a 3- to 6-membered carbocyclic ring or a 5- to 10-membered partially unsaturated carbocyclic ring.

In another embodiment Ln1 is supported on silica gel, dendrimers, polystyrenes or mesoporous siliceous foam, For example as described in Haraguchi, N., Tsuru, K., Arakawa, Y., Isuno, S. Org. Biomol. Chem. 2009, 7, 69.

In an embodiment, M is rhodium, ruthenium, iridium, platinum, palladium, iron or nickel.

In another embodiment, M is rhodium, ruthenium, iridium, or platinum.

In another embodiment, M is rhodium, ruthenium, or platinum.

In another embodiment, M is rhodium, iridium, or platinum.

In another embodiment, M is rhodium, ruthenium, or iridium.

In another embodiment, M is rhodium or ruthenium.

In another embodiment, M is rhodium or iridium.

In another embodiment, M is ruthenium or iridium.

In another embodiment, M is palladium, iron or nickel.

In another embodiment, M is palladium or nickel.

In another embodiment, M is, iron or nickel.

In another embodiment, M is palladium or iron.

In a preferred embodiment, M is rhodium.

In another preferred embodiment, M is ruthenium.

In another preferred embodiment, M is iridium.

In another preferred embodiment, M is palladium.

In another preferred embodiment, M is iron.

In another preferred embodiment, M is nickel.

In another preferred embodiment, M is platinum.

In another embodiment, m is 1 and MXLn($\eta$-arene)$_m$ is of the formula MXLnCp*, wherein M is rhodium, ruthenium, iridium, platinum, palladium, iron or nickel.

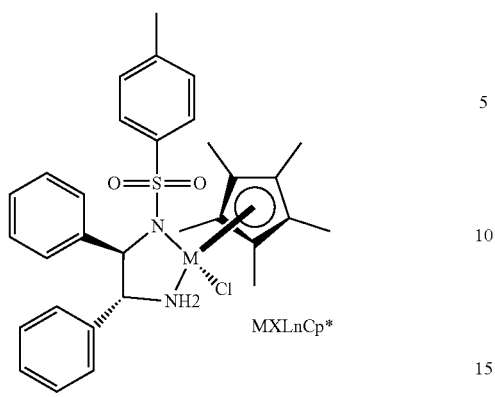

MXLnCp*

In another embodiment, Ln is Ln2 which is achiral phosphorous ligand.

In another embodiment, the chiral phosphorous ligand Ln2 is selected from chiral monodentate or bidentate, phosphine or phosphite ligands.

In another embodiment, the chiral phosphorous ligand is selected from ligands listed in below Table A or selected from their corresponding enantiomers.

TABLE A wherein Cy = cyclohexyl and Ph = phenyl

| Sr. No. | Structure | Name |
|---|---|---|
| 1. | 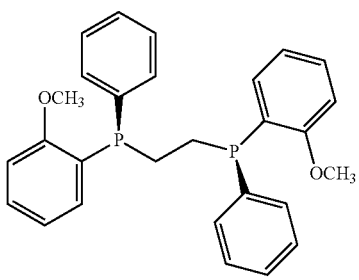 [SMILES: COc1ccccc1[P@](CC[P@](c1ccccc1)c1ccccc1OC)c1ccccc1] | (R,R)-DIPAMP |
| 2. | 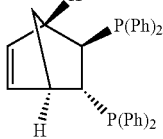 | (R,R)-NORPHOS |
| 3. | 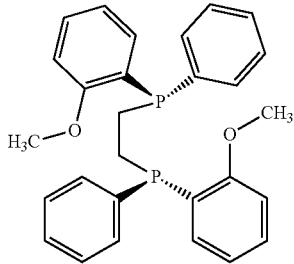 | (S,S)-DIPAMP |

TABLE A-continued wherein Cy = cyclohexyl and Ph = phenyl

| Sr. No. | Structure | Name |
|---|---|---|
| 4. | 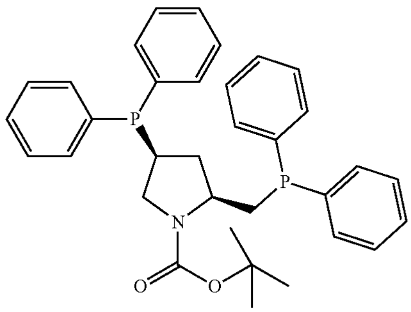 [SMILES: CC(C)(C)OC(=O)N1C[C@@H](P(c2ccccc2)c2ccccc2)C[C@H]1CP(c1ccccc1)c1ccccc1] | (S,S)-BPPM |
| 5 | 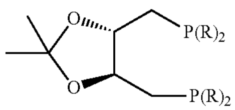 | (S,S)-DIOP: R = Ph<br>(S,S)-Cy-DIOP: R = Cy<br>(S,S)-MOD-DIOP:<br>R = 3,5-$(CH_3)_2$-4-$(CH_3O)C_6H_2$ |
| 6 | 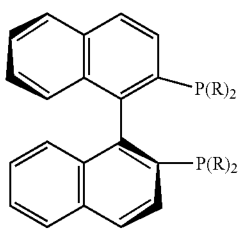 | (S)-BINAP: R = Ph<br>(S)-TolBINAP:<br>R = 4-$CH_3C_6H_4$<br>(S)-XylBINAP:<br>R = 3,5-$(CH_3)2$—$C_6H_3$ |
| 7 | 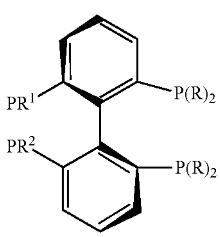 | (S)-BICHEP: R = Cy; $R^1$ = $CH_3$<br>(S)-BIPHEMP:<br>R = Ph; $R^1$ = $CH_3$<br>(S)-BIPHEP:<br>R = Ph; $R^1$ = $OCH_3$ |
| 8 | 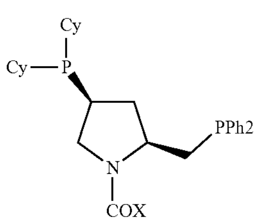 | (S,S)BCPM: X = $OC(CH_3)_3$<br>(S,S)-MCCPM:<br>X = $NHCH_3$ |
| 9 | 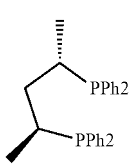 | (S,S)-BDPP |
| 10 | 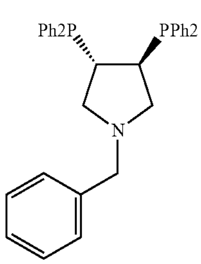 | (S,S)-PYRPHOS |

TABLE A-continued wherein Cy = cyclohexyl and Ph = phenyl

| Sr. No. | Structure | Name |
|---|---|---|
| 11 | 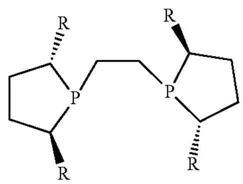 | (S,S)-Me-BPE: R = CH$_3$<br>(S,S)-Et-BPE: R = C$_2$H$_5$<br>(S,S)-iPr-BPE: R = iso-(CH$_3$)$_3$ |
| 12 | 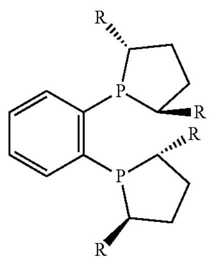 | (S,S)-Me-DuPhos: R = CH$_3$<br>(S,S)-Et-DuPhos: R = C$_2$H$_5$<br>(S,S)-iPr-DuPhos: R = iso-(CH$_3$)$_3$ |
| 13 | 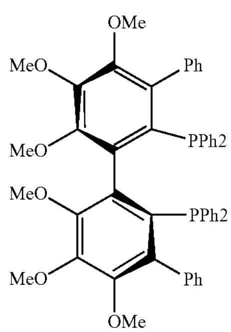 | (S)-o-Ph-Hex-aMeO-BIPHEP |
| 14 | 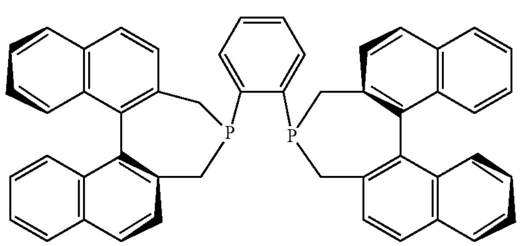 | (S,S)BINAPHANE |
| 15 | 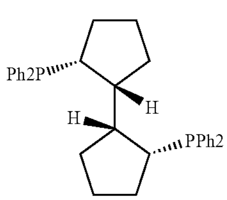 | (R,R)-BCIP |
| 16 | 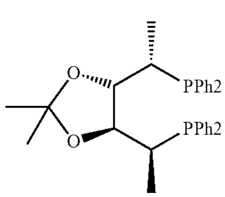 | (R,S,S,R)-DIOP* |

TABLE A-continued wherein Cy = cyclohexyl and Ph = phenyl

| Sr. No. | Structure | Name |
|---|---|---|
| 17 | 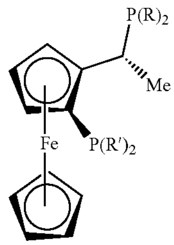 | (R)-(S)-Josi-phos: R = Cy, R' = Ph<br>(R)-(S)-PPF—t-Bu$_2$: R = t-Bu, R' = Ph<br>(R)-(S)-Xyliphos: R = 3,5-Me$_2$—C$_6$H$_3$, R' = Ph<br>(R)-(S)-Cy$_2$PF—PCy$_2$: R = R' = Cy |
| 18 | 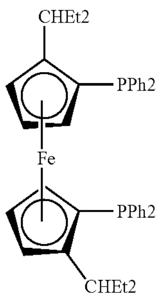 | (S,S)-FerroPHOS |
| 19 | 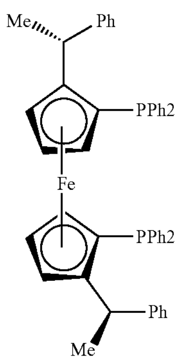 | FERRIPHOS |
| 20 | 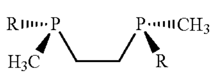 | (S,S)-BisP*<br>(S,S)-tBu-BisP*: R = tBu<br>(S,S)-Ad-BisP*: R = 1-ad-amantyl<br>(S,S)-Cy-BisP*: R = Cy |
| 21 | 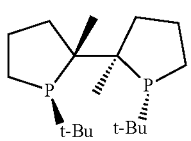 [SMILES: CC(C)(C)[P@@]1CCC[C@]1(C)[C@@]1(C)CCC[P@]1C(C)(C)C] | (S,S,R,R)-TangPhos |
| 22 | 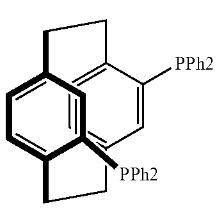 | (S)-[2,2]-PHENOPHOS |

TABLE A-continued wherein Cy = cyclohexyl and Ph = phenyl

| Sr. No. | Structure | Name |
|---|---|---|
| 23 | 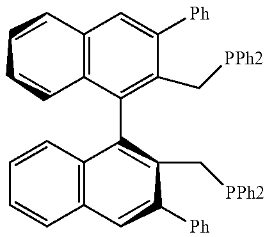 | (S)-Ph-o-NAPHOS |
| 24 | 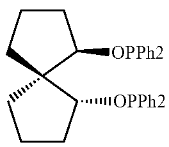 | (R)-spirOP |
| 25 | 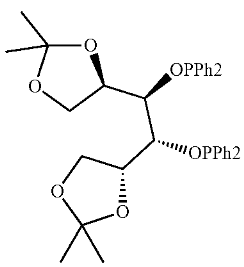 | DIMOP |
| 26 | 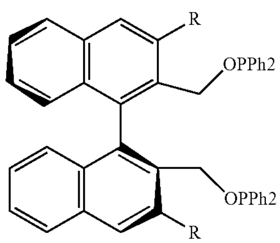 | BINAPO: R = H<br>(S)-Ph-o-BIN-APO;<br>R = Ph |
| 27 | 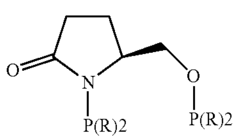 | (S)-Cy,Cy-ox-oProNOP:<br>R = Cy<br>(S)-Cp,Cp-ox-oProNOP:<br>R = Cp |
| 28 | 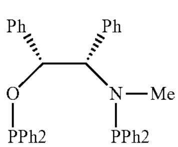 | (1R,2S)-DPAMPP |
| 29 | 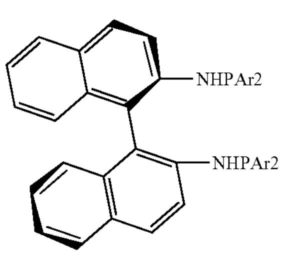 | (R)-BDPAB:<br>Ar = Ph<br>(R)-Xyl-BDP:<br>Ar = 3,5-Me$_2$C$_6$H$_3$ |

TABLE A-continued wherein Cy = cyclohexyl and Ph = phenyl

| Sr. No. | Structure | Name |
|---|---|---|
| 30 | (structure with NHPPh2 groups on octahydro-binaphthyl backbone) | (R)-H8-BDPAB |

In another embodiment, the chiral phosphorous ligand is selected from (R)-BINAP, (S)-BINAP, (R)TolBINAP, (S)-TolBINAP, (R,R)-DIPAMP, (S,S)-DIPAMP, (R)—(S)-Josiphos, or selected from their corresponding enantiomers.

In an embodiment, molar ratio of the compound of formula II to $MXLn(\eta\text{-arene})_m$ is in the range of 1:0.0001 to 1:0.001.

In a preferred embodiment, molar ratio of the compound of formula II to $MXLn(\eta\text{-arene})_m$ is in the range of 1:0.001 to 1:0.01.

In amore preferred embodiment, molar ratio of the compound of formula I to $MXLn(\eta\text{-arene})_m$ is in the range of 1:0.001 to 1:0.05.

In an embodiment, reaction temperature of the hydrogenation in step (D) is kept within a range of from 0 to 120° C., preferably in the range of from 0 to 85° C., preferably in the range of from 20 to 85° C., more preferably in the range of from 20° to 50° C., also more preferably in the range of from 0° to 30° C., also more preferably at 0° C.

In an embodiment, reaction of the hydrogenation in step (A) is carried out at a temperature below 0° C.

In an embodiment, the hydrogenation in step (D) is carried out in the absence of solvent.

In another embodiment, the hydrogenation in step (D) is carried out in a solvent.

Suitable solvents include water and aliphatic hydrocarbons such as pentane, hexane, cyclohexane and petroleum ether; aromatic hydrocarbons such as toluene, o-, m- and p-xylene; halogenated hydrocarbons such as methylene chloride, chloroform, 1,2-dichloroethane and chlorobenzene; alcohols such as methanol, ethanol, n-propanol, isopropanol, n-butanol and tert-butanol; $C_2$-$C_4$-alkandiols, such as ethylene glycol or propylene glycol; ketones such as acetone, 2-butanone; ether alkanols such as diethylene glycol; carboxylic esters such as ethyl acetate; N-methylpyrrolidone; dimethylformamide; dimethyl acetamide; and ethers including open-chained and cyclic ethers, especially diethyl ether, methyl-tert-butyl-ether (MTBE), 2-methoxy-2-methylbutane, cyclopentylmethylether, 1,4-dioxane, tetrahydrofuran, and 2-methyltetrahydrofuran, in particular tetrahydrofuran, MTBE, and 2-methyltetrahydrofuran. Mixtures of said solvents can also be used.

In a preferred embodiment, solvent is selected from water, $C_2$-$C_6$-alkandiols, $C_1$-$C_6$-haloalkanes, halobenzene, carboxylic esters, N-methylpyrrolidone; dimethylformamide; toluene, dimethyl acetamide and ethers including open-chained and cyclic ethers, or mixture of the two or more thereof.

In another preferred embodiment, solvent is selected from water, dimethylformamide, tetrahydrofuran, N-methylpyrrolidone, dimethyl acetamide or mixture of the two or more thereof.

In an embodiment, the volume ratio of the compound of formula VI to the solvent is in the range of 1:40 to 1:0.

In another embodiment, the volume ratio of compound of formula VI to the solvent is in the range of 1:30 to 1:5.

In a preferred embodiment, the volume ratio of compound of formula VI to the solvent is in the range of 1:20 to 1:10, preferably 1:1.

The reaction times in the step (D) may vary over a broad range. Preferred reaction times are in the range of 5 mins to 1 day, preferably from 15 mins to 6 hours, more preferably in the range of from 15 mins. to 3 hours, e.g. 1 to 2 hours.

In an embodiment, the step (D) can be carried out in the presence of surfactants $N(R^s)_4X^a$ wherein $R^s$ is independently $C_1$-$C_{22}$ alkyl, $C_1$-$C_{22}$ cycloalkyl, or aryl which is unsubstituted or substituted with halogen, and $X^a$ is chloro, bromo, iodo, hydrogen sulfate, phosphate, hexafluorophosphate, acetate, benzoate or tetrafluoroborate.

It is further preferred that the reaction is performed in a protective or inert gas atmosphere, e.g. under nitrogen or Argon.

It is further preferred that the reaction is performed under reduced pressure.

In another embodiment the reaction is performed under hydrogen atmosphere.

In a preferred embodiment, the compound of formula VII obtained by step (D) in >80% enantiomeric excess.

In the following, preferred embodiments regarding step (E) of the invention are provided. It is to be understood that the preferred embodiments mentioned above and those still to be illustrated below of step (E) of the invention are to be understood as preferred alone or in combination with each other.

In an embodiment, the step (E) is carried out in the presence of a base; Suitable bases are, in general, inorganic compounds, such as alkali metal and alkaline earth metal hydroxides, such as lithium hydroxide, sodium hydroxide, potassium hydroxide and calcium hydroxide, alkali metal and alkaline earth metal oxides, such as lithium oxide, sodium oxide, calcium oxide, and magnesium oxide, alkyl oxides of alkali metal and alkaline earth metal, such as sodium methylate, potassium methylate, sodium ethylate, potassium ethylate, sodium tert-butoxide, and potassium tert-butoxide, alkali metal and alkaline earth metal carbonates, such as lithium carbonate, potassium carbonate and calcium carbonate, and also alkali metal bicarbonates, such as sodium bicarbonate, moreover organic bases, for example tertiary amines, such as trimethylamine, triethylamine, triisopropylethylamine, N-methylmorpholine and N-methylpiperidine, pyridine, substituted pyridines, such as collidine, lutidine and 4-dimethylaminopyridine, and also bicyclic amines, such as 1,8-Diazabicyclo[5.4.0]undec-7-ene and 1,4-diazabicyclo[2.2.2]octane In one particularly preferred embodiment, the base is selected from alkali metal and alkaline earth metal hydroxides, in particular from the group consisting of lithium hydroxide, sodium hydroxide, magnesium hydroxide, potassium hydroxide, and calcium hydroxide.

In another particularly preferred embodiment, the base is selected from alkali metal and alkaline earth metal oxides, in particular from the group consisting of lithium oxide, sodium oxide, calcium oxide, and magnesium oxide.

In another particularly preferred embodiment, the base is selected from alkali metal and alkaline earth metal carbonates, in particular from the group consisting lithium carbonate and calcium carbonate.

In another particularly preferred embodiment, the base is selected from alkali metal bicarbonates, and is preferably sodium bicarbonate.

In another particularly preferred embodiment, the base is selected from alkali metal alkyls, in particular from the group consisting of methyllithium, butyllithium, and phenyllithium.

In another particularly preferred embodiment, the base is selected from alkylmagnesium halides, and is preferably isopropylmagnesiumchloride.

In another particularly preferred embodiment, the base is selected from trimethylamine, triethylamine, triisopropylethylamine, n-tributylamine and N-methylpiperidine, pyridine, substituted pyridines, such as collidine, lutidine and 4-dimethylaminopyridine, and also bicyclic amines.

In more particularly preferred embodiment, the base is n-tributylamine or triethylamine.

The bases are generally employed in equimolar amounts; however, they can also be used in catalytic amounts, in excess or, if appropriate, as solvent.

In an embodiment, the reaction temperature hydrolysis in step (C) is kept within a range of from 0 to 120° C., preferably in the range of from 20 to 85° C., more preferably in the range of from 20° to 60° C.

In an embodiment step (E) is carried out in the absence of solvent.

In another embodiment, the step (E) is carried out in a solvent.

Suitable solvents include water and aliphatic hydrocarbons such as hexane, cyclohexane and petroleum ether; aromatic hydrocarbons such as toluene, o-, m- and p-xylene; halogenated hydrocarbons such as methylene chloride, chloroform, 1,2-dichloroethane and chlorobenzene; alcohols such as methanol, ethanol, n-propanol, isopropanol, n-butanol, iso-butanol and tert-butanol; $C_2$-$C_4$-alkandiols, such as ethylene glycol or propylene glycol; ether alkanols such as diethylene glycol; ketones such as acetone or 2-butanone; carboxylic esters such as ethyl acetate; carboxylic amides such as N-methylpyrrolidone; dimethylformamide; and ethers including open-chained and cyclic ethers, especially diethyl ether, methyl-tert-butyl-ether (MTBE), 2-methoxy-2-methylbutane, cyclopentylmethylether, 1,4-dioxane, tetrahydrofuran, and 2-methyltetrahydrofuran, in particular tetrahydrofuran, MTBE, and 2-methyltetrahydrofuran. Mixtures of said solvents can also be used.

In another embodiment, the solvent is selected from $C_1$-$C_6$-alcohol, water, $C_2$-$C_6$-alkandiols, carboxylic esters, N-methylpyrrolidone, dimethylformamide, and ethers including open-chained and cyclic ethers, or mixture of the two or more thereof.

In another embodiment, the solvent is selected from water, dimethylformamide, N-methylpyrrolidone, methyl-tert-butyl-ether, methanol, ethanol, isopropanol, or mixture of two or more thereof.

Preferred solvents are protic solvents, preferably alcohols selected from the group consisting of such as methanol, ethanol, n-propanol, isopropanol, n-butanol and tert-butanol.

In a preferred embodiment, the solvent is a $C_1$-$C_4$-alcohol, in particular ethanol.

In an embodiment, the volume ratio of the compound of formula VII to solvent is in the range of 1:30 to 1:0.

In another embodiment, the volume ratio of the compound of formula VII to solvent is in the range of 1:20 to 1:5.

In a preferred embodiment, the volume ratio of the compound of formula VII to solvent is in the range of 1:20 to 1:10.

In the following, preferred embodiments regarding step (F) of the invention are provided. It is to be understood that the preferred embodiments mentioned above and those still to be illustrated below of step (F) of the invention are to be understood as preferred alone or in combination with each other.

In an embodiment, LG is $OR^u$;
In another embodiment, LG is $SR^u$;
In another embodiment, $R^u$ is unsubstituted $C_1$-$C_6$-alkyl;
In another embodiment, $R^u$ is $C_1$-$C_6$-alkyl, which is substituted with halogen;
In another embodiment, $R^u$ is unsubstituted aryl;
In another embodiment, $R^u$ is aryl which is substituted with halogen;

In an embodiment, the reaction temperature in step (F) is kept within a range of from 20 to 130° C., preferably in the range of from 20 to 100° C., more preferably in the range of from 70° to 100° C.

In an embodiment step (F) is carried out in the absence of solvent.

In another embodiment step (F) is carried out in a solvent.

Suitable solvents include aliphatic hydrocarbons such as hexane, heptane, cyclohexane and petroleum ether; aromatic hydrocarbons such as toluene, o-, m- and p-xylene; halogenated hydrocarbons such as methylene chloride, chloroform, 1,2-dichloroethane and chlorobenzene; alcohols such as methanol, ethanol, n-propanol, isopropanol, n-butanol and tert-butanol; $C_2$-$C_4$-alkandiols, such as ethylene glycol or propylene glycol; ketones such as acetone or 2-butanone; ether alkanols such as diethylene glycol; carboxylic esters such as ethyl acetate; N-methylpyrrolidone; dimethylformamide; and ethers including open-chained and cyclic ethers, especially diethyl ether, methyl-tert-butyl-ether (MTBE), 2-methoxy-2-methylbutane, cyclopentylmethylether, 1,4-dioxane, tetrahydrofuran, and 2-methyltetrahydrofuran, in particular tetrahydrofuran, MTBE, and 2-methyltetrahydrofuran. Mixtures of said solvents can also be used.

In another embodiment, the solvent is selected from dimethylformamide, N-methylpyrrolidone, toluene, xylene, monochlorobenzene, or mixture of two or more thereof.

Preferred solvents are aromatic hydrocarbons, preferably toluene, o-, m- and p-xylene, monochlorobenzene In a preferred embodiment, the solvent is toluene.

In an embodiment, the volume ratio of reactants to solvent is in the range of 1:40 to 1:0.

In another embodiment, the volume ratio of reactants to solvent is in the range of 1:40 to 1:5.

In a preferred embodiment, the volume ratio of reactants to solvent is in the range of 1:30 to 1:10.

In a preferred embodiment, the volume ratio of reactants to solvent is in the range of 1:20 to 1:10, preferably 1:5.

In a preferred embodiment, the compound of formula X obtained by step (F) in >95% enantiomeric excess.

In another embodiment of the invention, a process for preparing a compound of formula X having below stereochemistry as in formula X—R or a process for preparing a compound of formula X with enantiomeric excess of R-enantiomer i.e. compound X—R,

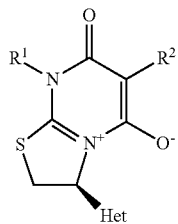

X-R wherein Het, R¹ and R² are as defined herein;
comprising at least the steps of,
(A) reacting a compound of formula III,

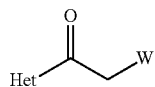

III wherein Het and W are as defined herein;
with $M^2OR^{AC}$, wherein $M^2$ and $R^{AC}$ are as defined herein;
to obtain the compound of formula IV,

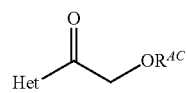

IV wherein Het and $R^{AC}$ are as defined herein;
(B) hydrolyzing the compound of formula IV as defined herein in the presence of an acid or a base to obtain a compound of formula V,

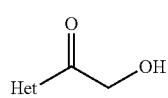

V wherein Het is as defined in compound of formula IV;
(C) reacting the compound of formula V with $X^1SO_2NH_2$, wherein $X^1$ is halogen; to obtain the compound of formula VI,

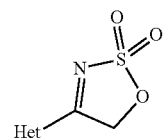

VI wherein Het is as defined in compound of formula V.
(D) hydrogenation of the compound of formula VI, in the presence of a hydrogenation catalyst MXLnCp* wherein M is rhodium, ruthenium, iridium, palladium, iron, platinum, or nickel,

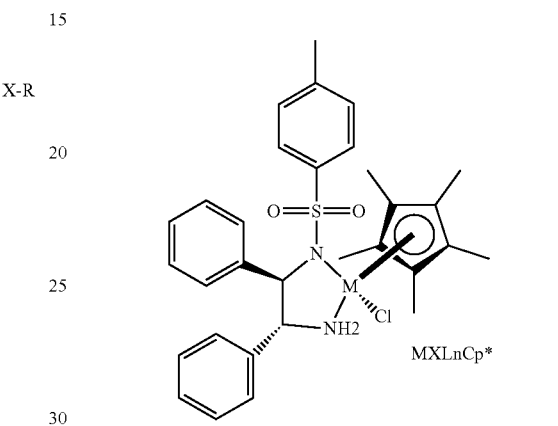

MXLnCp* and a hydrogen source selected from a) hydrogen, b) mixture of $N(R)_3$ wherein R is H or $C_1$-$C_6$-alkyl, and HCOOH, c) HCOONa or HCOOK, d) mixture of $C_1$-$C_8$-alcohol and t-BuOK, t-BuONa, or t-BuOLi, and e) combination of two or more from a) to d);
to obtain a compound of formula VII having below stereochemistry as in formula VII-R,

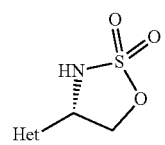

VII-R wherein Het is as defined in the compound of formula VI;
(E) reacting the compound of formula VII-R with R¹NCS, wherein R¹ is as defined herein, in the presence of a base, to obtain a compound of formula VIII having below stereochemistry as in formula VIII-R,

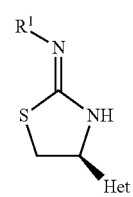

VIII-R wherein Het and R¹ are as defined in the compound of formula VII-R;
(D) reacting the compound of formula VIII-R with a compound of formula IX,

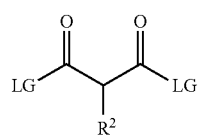

IX wherein LG and R² are as defined herein,
to obtain the compound of formula X—R.

EXAMPLES

The characterization can be done by coupled High Performance Liquid Chromatography/mass spectrometry (HPLC/MS), Gas chromatography (GC), by NMR or by their melting points.

HPLC method: Agilent Eclipse Plus C18, 150 mm×4.6 mm ID×5 um
Gradient A=0.1% TFA in Water, B=0.1% TFA in Acetonitrile.
Flow=1.4 ml/min., column oven temperature=30 C
Gradient program=10% B—100% B—5 min, hold for 2 min, 3 min—10% B.
Run Time=10 min
LCMS method 1: C18 Column (50 mm×3.0 mm×3µ)
Gradient A=10 Mm Ammonium formate in water, B=0.1% Formic acid in acetonitrile
Flow=1.2 ml/min., column oven temperature=40° C.
Gradient program=10% B to 100% B in 1.5 min., hold for 1 min 100% B, 1 min—10% B
Run time: 3.75 min
Chiral HPLC method 1: ChiralPak IA column, 150 mm×4.6 mm×5µ
Mobile phase A=heptane, B=isopropanol,
Flow=1.0 ml/min, column oven temperature=40° C.
Gradient program=10% B Isocratic; run time: 20 min
Chiral HPLC method 3: ChiralPak IA column, 150 mm×4.6 mm×5µ
Mobile phase A=heptane, B=isopropanol,
Flow=1.0 ml/min, column oven temperature=40° C.
Gradient program=40% B Isocratic; run time: 20 min
¹H-NMR: The signals are characterized by chemical shift (ppm) vs. tetramethylsilane, by their multiplicity and by their integral (relative number of hydrogen atoms given). The following abbreviations are used to characterize the multiplicity of the signals: m=multiplet, q=quartet, t=triplet, d=doublet and s=singlet.
Abbreviations used are: h for hour(s), min for minute(s), rt for retention time and ambient temperature for 20-25° C.

The present invention is now illustrated in further details by the following examples, without imposing any limitation thereto.

With appropriate modification of the starting materials, the procedures as described in the examples below can be used to obtain further compounds of formula V, VI, VII, VIII, or X.

Example-1: Preparation of (3R)-3-(2-chlorothiazol-5-yl)-8-methyl-7-oxo-6-phenyl-2,3-dihydrothiazolo[3,2-a]pyrimidin-4-ium-5-olate Step-1: Preparation of 2-chloro-N-methoxy-N-methyl-acetamide A 3 L four necked flask equipped with Teflon-blade stirrer, reflux condenser and thermo-pocket was charged with N-methoxymethanamine hydrochloride (345 g), water (1.6 litre) and the resulting reaction mixture was cooled to 0 to −5° C. Then potassium carbonate (1466 g) was added in lots to the above reaction mixture followed by the addition of methyl tert-butyl ether (1.4 litre). The chloroacetyl chloride (400 g) was dissolved in tert-butyl methyl ether (0.2 litre) and added dropwise in to the above kept reaction mixture at −5° C. to 0° C. and the reaction mixture was stirred for 2 h at 0° C. The reaction mixture was allowed to come to ambient temperature and two phases were separated. The organic layer was dried over sodium sulfate, filtered and evaporated to provide 2-chloro-N-methoxy-N-methyl-acetamide as white solid (440 g, 90% yield and 98.0% area purity by HPLC).

Step-2: Preparation of 2-chloro-1-(2-chlorothiazol-5-yl)ethenone

A 5 L, four necked flask equipped with Teflon-blade stirrer, reflux condenser and thermo-pocket was charged with 2-chlorothiazole (250 g), TH F (0.75 L) and the resulting reaction mixture was cooled to 0 to −5° C. Then isopropylmagnesium chloride lithium chloride (1.929 L, 1.3 M solution in THF) was added over 0.5 h into the above kept reaction mixture at 0 to −5° C. The reaction mixture was then heated to 40° C. and the reaction was continued at 40° C. for 2 h. The formation of chloro-(2-chlorothiazol-5-yl) magnesium species was confirmed by quenching the small aliquot of the reaction mixture with iodine and monitoring the formation of 2-chloro-5-iodothiazole by GC analysis (96% conversion was observed by GC analysis). The reaction mixture was cooled to 0 to −5° C. and the solution of 2-chloro-N-methoxy-N-methyl-acetamide (343 g) in THE (0.25 L) was added dropwise. The reaction was continued at -5 to 0° C. for 1 h and the reaction progress was monitored by HPLC. The reaction mixture was quenched with 1.5 N aq. HCl solution (1 L) at -5 to 0° C. and then warmed to ambient temperature. The two phases were separated and the aqueous phase extracted with methyl tert-butyl ether (2×300 mL). The combined organic layers were dried over sodium sulfate, filtered and evaporated to obtain crude residue. The crude product was dissolved in methyl tert-butyl ether (0.7 L) at ambient temperature and activated charcoal (4 g) and silica (80 g, 60-120 mesh) were added. The slurry was stirred for 0.5 h, filtered through Buchner funnel and washed with methyl tert-butyl ether (0.3 L). The filtrate was evaporated to obtain 2-chloro-1-(2-chlorothiazol-5-yl)ethanone as pale brown colored oil (409 g, 46% area purity by HPLC)

Step-3: Preparation of [2-(2-chlorothiazol-5-yl)-2-oxo-ethyl] acetate

A 0.25 L, three necked flask equipped with teflon-blade stirrer, reflux condenser and thermo-pocket was charged with 2-chloro-1-(2-chlorothiazol-5-yl)ethanone (15 g, 46 area % HPLC purity) and dimethylformamide (45 mL) at ambient temperature. Then sodium acetate (12.55 g) was added in portions and reaction was continued at ambient temperature for 4 h. The reaction progress was monitored by HPLC (>95% conversion by HPLC). The reaction was quenched with water (50 mL) and extracted with methyl tert-butyl ether (3×100 mL). The two phases were separated and the combined organic phases were dried over sodium sulfate, filtered and evaporated to obtain crude residue (17 g). The crude product was purified by silica gel column chromatography to obtain [2-(2-chlorothiazol-5-yl)-2-oxo-ethyl] acetate as yellow colored solid (7.5 g).

Step-4: Preparation of 1-(2-chlorothiazol-5-yl)-2-hydroxy-ethanone

A 250 mL, three necked flask equipped with magnetic stirrer, reflux condenser and thermo-pocket was charged with [2-(2-chlorothiazol-5-yl)-2-oxo-ethyl] acetate (7.5 g) and 1 N HCl in MeOH (50 mL). The resulting solution was stirred for 5 h and reaction progress was monitored by TLC. The methanol from reaction mixture was distilled under vacuum and crude residue obtained was purified by column chromatography to obtain 1-(2-chlorothiazol-5-yl)-2-hydroxy-ethanone as pale yellow solid (2.8 g, 84% area purity by HPLC).

Step-5: Preparation of 4-(2-chlorothiazol-5-yl)-5H-oxathiazole 2,2-dioxide

A 100 mL, three neck flasks equipped with magnetic stirrer, reflux condenser and thermo-pocket was charged with 1-(2-chlorothiazol-5-yl)-2-hydroxy-ethanone (1 g), toluene (20 mL), chlorosulfonamide (0.975 g) and p-toluenesulfonic acid (0.214 g). The resulting solution was heated to 100° C. and stirred for 1 h. The reaction progress was monitored by HPLC (>95% conversion). The reaction mixture was quenched with water and extracted with MTBE (15 mL×2). The two phases were separated, organic phase was evaporated and purified by column chromatography 4-(2-chlorothiazol-5-yl)-5H-oxathiazole 2,2-dioxide (0.42 g).

Step-6: Preparation of (4R)-4-(2-chlorothiazol-5-yl) oxathiazolidine 2,2-dioxide a) Preparation of Rhodium Catalyst—RhCl[(R,R)-TsDPEN]Cp*:
A 250 mL, three necked flask equipped with teflon-blade stirrer, nitrogen inlet and thermo-pocket was charged with [RhCl$_2$Cp*]$_2$ (2.0 g), (1R,2R)—N-p-toluenesulfonyl-1,2-diphenylethylenediamine (2.38 g), dichloromethane (68 mL) and triethylamine (1.72 ml) under nitrogen atmosphere. The resulting slurry was stirred for 0.5 h at 22-27° C. and distilled water was added (40 mL). The two phases were separated and the organic phase was washed with water (40 mL). The organic phase was dried over sodium sulfate, filtered and evaporated to get brown coloured solid residue. The brown residue was triturated with n-heptane (20 mL), filtered and dried under nitrogen atmosphere to get obtain RhCl [(R, R)-TsDPEN]Cp* as red coloured solid (3.4 g).

b) Preparation of HCOOH-NEt$_3$ Mixture:
In a 2 liter, 3 neck round bottom flask Formic acid (275 mL, >=99% w/w) was added and cooled to 0° C. To this, triethylamine 250 mL, >=99% w/w) was added slowly at 0° C. and used immediately in reaction.

c) Preparation of (4R)-4-(2-chlorothiazol-5-yl)oxathiazolidine 2,2-dioxide:
A 100 ml, two necked flask equipped with magnetic stirrer, condenser and thermo-pocket was charged with 4-(2-chlorothiazol-5-yl)-5H-oxathiazole 2,2-dioxide (0.5 g) and dimethylformamide (15 mL, 30V) was degassed with nitrogen for 10 min. Then RhCl[(R,R)-TsDPEN]Cp* (27 mg) was added followed by dropwise addition of HCOOH-NEt$_3$ (2.5 mL, in a ratio of 5:2). The resulting mixture was stirred for 2 h. The HPLC showed >97% conversion. The reaction mixture was quenched with water (15 ml) and extracted with methyl tert-butyl ether (3×50 mL). The combined organic phase was evaporated to obtain (4R)-4-(2-chlorothiazol-5-yl)oxathiazolidine 2,2-dioxide (500 mg; 90 area % HPLC purity (rt=3.645 min.), >99% ee by chiral HPLC method 1).

Step-7: Preparation of (4R)-4-(2-chlorothiazol-5-yl)-N-methyl-thiazolidin-2-imine A 100 mL, three necked flask equipped with magnetic stirrer, reflux condenser and thermo-pocket was charged with (4R)-4-(2-chlorothiazol-5-yl)oxathiazolidine 2,2-dioxide (0.5 g, with 99% ee), ethanol (2 ml), methyl isothiocyanate (0.228 g) and triethylamine (0.56 ml) at ambient temperature. The resulting mixture was stirred for 14 h at 22-27° C. Then organic volatiles were removed under vacuum and sodium hydroxide (0.2 g) and water (2 mL) were added into the reaction flask. The reaction mixture was heated to 100° C. and stirred for 2 h. The reaction was diluted with water (2 mL) and extracted with methyl tert-butyl ether (2×50 mL). The organic phases were dried over sodium sulfate and evaporated under vacuum to provide (4R)-4-(2-chlorothiazol-5-yl)-N-methyl-thiazolidin-2-imine as brown oil [0.34 g, m/z=234 amu (M+H$^+$)].

Step-8: Preparation of (3R)-3-(2-chlorothiazol-5-yl)-8-methyl-7-oxo-6-phenyl-2,3-dihydrothiazolo[3,2-a]pyrimidin-4-ium-5-olate A 50 mL, three necked flask equipped with magnetic stirrer, reflux condenser and thermo-pocket was charged with (E,4R)-4-(2-chlorothiazol-5-yl)-N-methyl-thiazolidin-2-imine (0.34 g), toluene (2 mL) and heated to 110° C. under nitrogen atmosphere. Then bis(2,4,6-trichlorophenyl) 2-phenylpropanedioate (0.857 g) was added in lots into the reaction mass kept at 110° C. After stirring at 110° C. for 2 h, H PLC showed >99% conversion. The reaction was cooled below 50° C. and the precipitated pale yellow colored solid was filtered through sintered funnel and then solid residue was washed with methyl tert-butyl ether (4 mL) and dried under vacuum to provide (3R)-3-(2-chlorothiazol-5-yl)-8-methyl-7-oxo-6-phenyl-2,3-dihydrothiazolo[3,2-a]pyrimidin-4-ium-5-olate (110 mg, m/z=378 amu (M+H+) & 95.2% enantiomeric excess by chiral HPLC method 3). $^1$H NMR (300 MHz, DMSO-d6): 3.42 (s, 3H), 3.94 (d, J=12 Hz, 1H), 4.25-4.32 (m, 1H), 6.48 (d, J=8.1 Hz, 1H), 7.06-7.11 (m, 1H), 7.21-7.26 (m, 2H), 7.6 (d, J=7.5 Hz, 1H), 7.96 (s, 1H).

Example-2: Preparation of (3R)-3-(2-chlorothiazol-5-yl)-8-methyl-7-oxo-6-phenyl-2,3-dihydrothiazolo [3,2-a]pyrimidin-4-ium-5-olate Step-1: Preparation of (4R)-4-(2-chlorothiazol-5-yl) oxathiazolidine 2,2-dioxide a) Preparation of HCOOH-NEt$_3$ mixture: prepared as described in step-4 of example 1.
b) Preparation of Preparation of (4R)-4-(2-chlorothiazol-5-yl)oxathiazolidine 2,2-dioxide:
A 1 L 3 neck round bottom flask, was charged with 4-(2-chlorothiazol-5-yl)-5H-oxathiazole 2,2-dioxide (50 g), dimethylformamide (100 ml), toluene (100 ml) and degassed with nitrogen for 10 min. Then pentamethylcyclopentadienyl rhodium chloride dimer (120 mg) & (1R,2R)—N-p-toluenesulfonyl-1,2-diphenylethylenediamine (136 mg) were added under nitrogen atmosphere at ambient temperature. The resulting mixture was cooled to 0 to 5° C. & freshly prepared HCOOHNEt$_3$ (12 mL, in a ratio of 1.1:1) was added & stirred for 2 h. The reaction was monitored by HPLC and quenched with water (100 mL) and extracted with Toluene (200 mL). The combined organic phase was washed with water (3×20 ml) and evaporated to obtain (4R)-4-(2-chlorothiazol-5-yl)oxathiazolidine 2,2-dioxide (49 g, 98% ee by chiral HPLC method 1).

Step-2: Preparation of (4R)-4-(2-chlorothiazol-5-yl)-N-methyl-thiazolidin-2-imine A 1 L, three necked flask equipped with magnetic stirrer, reflux condenser and thermo-pocket was charged with (4R)-4-(2-chlorothiazol-5-yl)oxathiazolidine 2,2-dioxide (49 g, with 98% ee), ethanol (196 ml), methyl isothiocyanate (22.5 g) and triethylamine (56 ml) at ambient temperature. The resulting mixture was stirred for 14 h at 22-27° C. Then organic volatiles were removed under vacuum and sodium hydroxide (0.2 g) and water (2 mL) were added into the reaction flask. The reaction mixture was heated to 70° C. and stirred for 2 h. The reaction was diluted with water (2 mL) and extracted with toluene (2×500 mL). The organic phases were dried over sodium sulfate and evaporated under vacuum to provide (4R)-4-(2-chlorothiazol-5-yl)-N-methyl-thiazolidin-2-imine as brown oil [44.7 g, m/z=234 amu (M+H+)].

Step-3: Preparation of (3R)-3-(2-chlorothiazol-5-yl)-8-methyl-7-oxo-6-phenyl-2,3-dihydrothiazolo[3,2-a]pyrimidin-4-ium-5-olate A 500 mL, three necked flask equipped with magnetic stirrer, reflux condenser and thermo-pocket was charged with (E,4R)-4-(2-chlorothiazol-5-yl)-N-methyl-thiazolidin-2-imine (35 g), toluene (70 mL) and heated to 80° C. under nitrogen atmosphere. Then bis(4-chlorophenyl) 2-phenyl-propanedioate (60 g) was dissolved in toluene (70 ml) at 45° C. and added drop wise into the reaction mass kept at 80° C. After stirring at 100° C. for 1 h, HPLC showed >99% conversion. The reaction was cooled below 50° C. and the precipitated pale yellow coloured solid was filtered, washed with toluene (3×70 mL) and dried under vacuum to provide (3R)-3-(2-chlorothiazol-5-yl)-8-methyl-7-oxo-6-phenyl-2,3-dihydrothiazolo[3,2-a]pyrimidin-4-ium-5-olate as 1 st lot (29 g, m/z=378 amu (M+H+) & 99% enantiomeric excess by chiral HPLC method 3); The combined mother liquor was transferred to reactor, acetone (105 ml) was added and stirred at 22-27° C. for 1 h. The precipitated pale yellow colored solid was filtered and washed with toluene (70 ml×3) to obtain (3R)-3-(2-chlorothiazol-5-yl)-8-methyl-7-oxo-6-phenyl-2,3-dihydrothiazolo[3,2-a]pyrimidin-4-ium-5-olate as $2^{nd}$ lot (13 g, 99 area % HPLC purity & 98.7% enantiomeric excess by chiral HPLC method 3).

The invention claimed is:

1. A process for preparing S-containing pyrimidinium compound of formula X

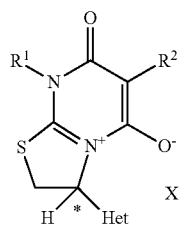

wherein

C* is an asymmetric carbon atom of S or R-configuration;

$R^1$ is $C_1$-$C_4$-alkyl, $C_3$-$C_6$-cycloalkyl, $C_2$-$C_4$-alkenyl, or —$CH_2$-phenyl, which groups are unsubstituted or substituted with halogen or $C_1$-$C_4$-alkyl;

$R^2$ is a 5- or 6-membered saturated, partially unsaturated or aromatic carbo- or heterocyclic ring, wherein the ring is unsubstituted or substituted with $R^{2a}$;

Het is selected from D-1, D-2, and D-3:

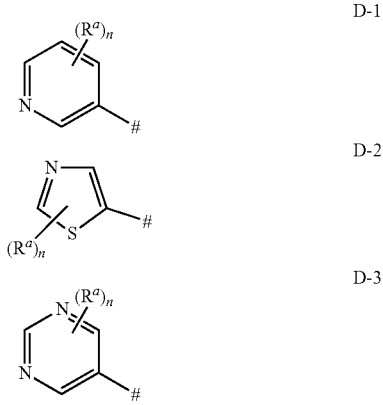

wherein $R^a$ is each independently $R^a$ is halogen, $C_1$-$C_4$-haloalkyl, $C_1C_4$-alkoxy, $C_1$-$C_4$-alkylthio, or phenyl;

n is 0, 1 or 2; and # denotes the bond in formula X;

$R^{2a}$ is halogen, $C_1$-$C_6$-haloalkyl, $C_1$-$C_6$-haloalkoxy, $OR^c$, $C(=O)OR^c$, $C(=O)NR^bR^c$, phenyl, or pyridyl, which is unsubstituted or substituted with halogen, $C_1$-$C_6$-haloalkyl or $C_1$-$C_6$-haloalkoxy;

$R^b$ is hydrogen, $C_1$-$C_6$-alkyl, $C_1$-$C_6$-haloalkyl, $C_1$-$C_6$-alkoxy, or $C_1$-$C_6$-haloalkoxy; and $R^c$ is hydrogen, $C_1$-$C_4$-alkyl, $C_1$-$C_4$-haloalkyl, or $C_1$-$C_6$ cycloalkyl;

wherein two geminally bound groups $R^cR^b$ together with the atom to which they are bound, may form a 3- to 7-membered saturated, partially unsaturated or aromatic heterocyclic ring;

comprising at least the step of, (E) reacting the compound of formula VII,

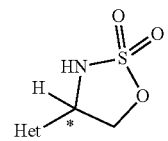

wherein

C* is an asymmetric carbon atom of S or R-configuration;

Het is as defined in compound of formula X;

with $R^1NCS$, wherein $R^1$ is $C_1$-$C_4$-alkyl, $C_3$-$C_6$-cycloalkyl, $C_2$-$C_4$-alkenyl or —$CH_2$-phenyl, which groups unsubstituted or substituted by halogen or $C_1$-$C_4$-alkyl;

in the presence of a base, to obtain a compound of formula VIII,

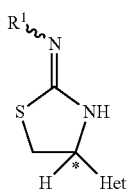
VIII wherein
C* and Het are as defined in the compound of formula VII;
R$^1$ is as defined herein;
and further reacting the compound of formula VIII to obtain the compound of formula X.

2. The process according to claim 1, further comprising at least the steps of,
(A) reacting a compound of formula III,

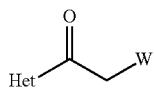
III wherein
W is halogen, O-p-toluenesulfonyl, O-methanesulfonyl, or O-trifluoromethanesulfonyl;
Het is as defined in compound of formula X in claim 1;
with M$^2$OR$^{AC}$ wherein M$^2$ is selected from lithium, sodium, potassium, aluminium, barium, caesium, calcium, and magnesium; R$^{AC}$ is C(=O)—C$_1$-C$_4$-alkyl;
to obtain the compound of formula IV,

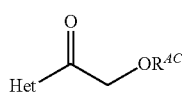
IV wherein Het and R$^A$c are as defined herein;
(B) hydrolyzing the compound of formula IV as defined herein in the presence of an acid or a base to obtain a compound of formula V,

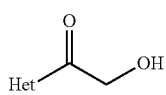
V wherein Het is as defined in compound of formula IV;
(C) reacting the compound of formula V with X$^2$SO$_2$NH$_2$ wherein X$^2$ is halogen, to obtain the compound of formula VI

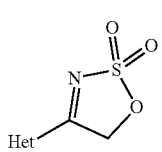
VI wherein Het is as defined in compound of formula V;
(D) hydrogenation of the compound of formula VI,
in the presence of a hydrogenation catalyst MXLn(η-arene)$_m$ wherein
η-arene is selected from benzene, p-cymene, mesitylene, 1,3,5-triethylbenzene, hexamethylbenzene, anisole, 1,5-cyclooctadiene, cyclopentadienyl (Cp), norbornadiene, pentamethylcyclopentadienyl (Cp*), and an aryl ring which is unsubstituted or substituted with C$_1$-C$_4$-alkyl;
M is a transition metal from group VIII to group XII of the periodic table;
X is an anion;
m is 0 or 1;
Ln is Ln1 or Ln2,
wherein
Ln1 is a chiral ligand of the formula Ln1,

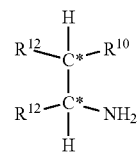
Ln1 wherein
C* is an asymmetric carbon atom of S or R-configuration;
R$^{10}$ is OH or NH—SO$_2$—R$^1$;
R$^{11}$ is aryl unsubstituted or substituted independently of each other with halogen, C$_1$-C$_{10}$-alkyl, C$_1$-C$_4$-alkoxy, C$_3$-C$_6$-cycloalkyl, SO$_3$H, or SO$_3$Na;
or
R$^1$ is C$_1$-C$_{10}$-perfluoroalkyl, or R$^{13}$R$^{14}$N wherein R$^{13}$ and R$^{14}$ independently represent C$_1$-C$_{10}$-alkyl unsubstituted or substituted with C$_6$-C$_{10}$-aryl, or R$^{13}$ and R$^{14}$ each independently represent a C$_6$-C$_{10}$-cycloalkyl;
R$^{12}$ independently represents aryl ring or C$_6$-C$_{10}$-cycloalkyl ring, wherein the ring is unsubstituted or substituted independently of each other with halogen, C$_1$-C$_{10}$-alkyl, C$_1$-C$_4$-alkoxy, C$_3$-C$_6$-cycloalkyl, SO$_3$H, or SO$_3$Na, or both R$^{12}$ are linked together to form a 3- to 6-membered carbocyclic ring or a 5- to 10-membered partially unsaturated carbocyclic ring;
Ln2 is a chiral phosphorous ligand;
and a hydrogen source selected from a) hydrogen, b) mixture of N(R)$_3$ wherein R is H or C$_1$-C$_6$-alkyl, and HCOOH, c) HCOONa or HCOOK, d) mixture of C$_1$-C$_8$-alcohol and t-BuOK, t-BuONa, or t-BuOLi, and e) combination of two or more from a) to d);
to obtain a compound of formula VII,

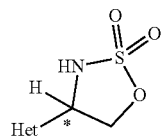
VII wherein
C* is an asymmetric carbon atom of S or R-configuration;
Het is as defined in compound of formula VI.

3. The process according to claim 1, wherein further reacting the compound of formula VIII comprises the step (F) of reacting the compound of formula VIII with a compound of formula IX,

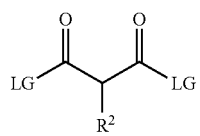

wherein,
LG is a leaving group selected from halogen, $OR^u$, and $SR^u$; wherein
$R^u$ is $C_1$-$C_6$-alkyl or aryl, which is unsubstituted or substituted with halogen;
$R^2$ is a 5- or 6-membered saturated, partially unsaturated or aromatic carbo- or heterocyclic ring, wherein the ring is unsubstituted or substituted with $R^{2a}$;
to obtain the compound of formula X.

4. The process according to claim 2, wherein η-arene is an aryl ring which is unsubstituted or substituted with $C_1$-$C_4$-alkyl.

5. The process according to claim 2, wherein η-arene is selected from benzene, p-cymene, mesitylene, 1,3,5-triethylbenzene, hexamethylbenzene, anisole, 1,5-cyclooctadiene, cyclopentadienyl (Cp), norbornadiene, and pentamethylcyclopentadienyl (Cp*).

6. The process according to claim 2, wherein $MXLn(η\text{-arene})_m$ in step (D) is $MXLn1(η\text{-arene})_m$ and wherein $R^{10}$ is $NH—SO_2—R^{11}$; and $R^{12}$ and $R^{11}$ independently are phenyl which are unsubstituted or substituted with 1 or 2 substituents selected from halogen, $C_1$-$C_4$-alkyl, $C_1$-$C_4$-alkoxy, $C_3$-$C_6$-cycloalkyl, $SO_3H$, and $SO_3Na$.

7. The process according to claim 2, wherein $MXLn(η\text{-arene})_m$ in step (D) is $MXLn1(η\text{-arene})_m$ and wherein X is halide; $R^{12}$ independently is phenyl, 2-methylphenyl, 3-methylphenyl, 4-methylphenyl or 4-methoxyphenyl; $R^{10}$ is $NH—SO_2—R^{11}$ and $—SO_2—R^{11}$ is p-toluenesulfonyl, 4-benzenesulfonyl, or pentafluorophenyl-sulfonyl.

8. The process according to claim 2, wherein m is 1 and $MXLn(η\text{-arene})_m$ in step (D) is of the formula MXLnCp*, wherein M is rhodium, ruthenium, iridium, palladium, iron, platinum, or nickel,

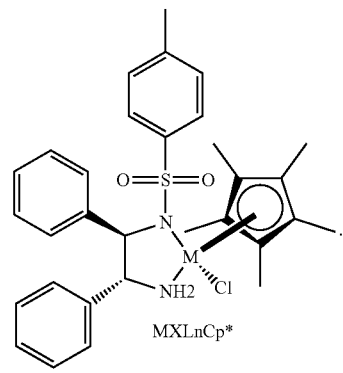

MXLnCp*

9. The process according to claim 2, wherein M in step (D) is rhodium, ruthenium, or iridium.

10. The process according to claim 1, wherein the base in step (E) is selected from triethylamine, diisopropylethyl amine, tri-nbutylamine, sodium hydroxide, and potassium hydroxide.

11. The process according to claim 1, wherein
$R^1$ is $C_1$-$C_4$-alkyl, $C_3$-$C_6$-cycloalkyl, or $C_2$-$C_4$-alkenyl, which is unsubstituted, or substituted with halogen.

12. The process according to claim 1, wherein
$R^2$ is phenyl, pyridinyl, or thiophenyl, which is unsubstituted or substituted by $R^{2a}$.

13. The process according to claim 1, wherein
$R^a$ is halogen or $C_1$-$C_4$-haloalkyl.

14. The process according to claim 1, wherein Het is D-2 wherein n is 0 and $R^a$ is halogen.

15. An optically active compound of formula VII

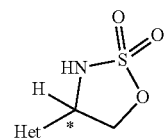

wherein
C* is an asymmetric carbon atom of S or R-configuration; and Het is selected from D-2 or D-3:

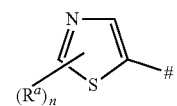

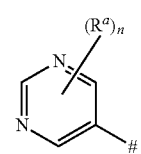

wherein
$R^a$ is each independently $R^a$ is halogen, $C_1$-$C_4$-haloalkyl, $C_1$$C_4$-alkoxy, $C_1$-$C_4$-alkylthio, or phenyl;
n is 0, 1 or 2; and
# denotes the bond in formula VII.

16. A process for preparing a compound of formula VIII

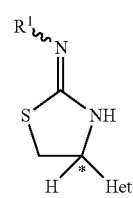

wherein
C* is an asymmetric carbon atom of S or R-configuration;
$R^1$ is $C_1$-$C_4$-alkyl, $C_3$-$C_6$-cycloalkyl, $C_2$-$C_4$-alkenyl, or —$CH_2$-phenyl, which groups are unsubstituted or substituted with halogen or $C_1$-$C_4$-alkyl; and
Het is selected from D-1, D-2, and D-3:

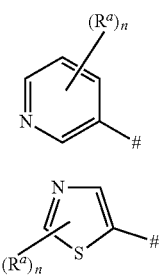

wherein $R^a$ is each independently $R^a$ is halogen, $C_1$-$C_4$-haloalkyl, $C_1$$C_4$-alkoxy, $C_1$-$C_4$-alkylthio, or phenyl;

n is 0, 1 or 2; and

\# denotes the bond in formula VIII;

comprising at least the step of, (E) reacting the compound of formula VII,

VII wherein

C* is an asymmetric carbon atom of S or R-configuration;

Het is as defined in compound of formula VIII;

with $R^1$NCS, wherein $R^1$ is $C_1$-$C_4$-alkyl, $C_3$-$C_6$-cycloalkyl, $C_2$-$C_4$-alkenyl or —$CH_2$-phenyl, which groups unsubstituted or substituted by halogen or $C_1$-$C_4$-alkyl;

in the presence of a base, to obtain the compound of formula VIII.

* * * * *